United States Patent [19]

Miljanich et al.

[11] Patent Number: 5,051,403

[45] Date of Patent: Sep. 24, 1991

[54] METHOD OF TREATING ISCHEMIA-RELATED NEURONAL DAMAGE

[75] Inventors: George P. Miljanich, Redwood City; Robert S. Bitner, Mountain View; Stephen S. Bowersox, Menlo Park; James A. Fox, Palo Alto; Karen L. Valentino, San Carlos; Donald H. Yamashiro, San Francisco, all of Calif.

[73] Assignee: Neurex Corporation, Menlo Park, Calif.

[21] Appl. No.: 440,094

[22] Filed: Nov. 22, 1989

[51] Int. Cl.[5] .......................... A61K 37/02; C07K 7/08; C07K 7/10

[52] U.S. Cl. .......................................... 514/12; 514/13; 514/14; 530/324; 530/325; 530/326

[58] Field of Search ............................ 514/12, 13, 14; 530/327, 324, 325, 326; 424/537

[56] References Cited

U.S. PATENT DOCUMENTS

| | | | |
|---|---|---|---|
| 4,447,356 | 5/1984 | Olivera et al. | 260/112.5 R |
| 4,925,664 | 5/1990 | Jackson et al. | 424/537 |
| 4,950,739 | 8/1990 | Cherksey et al. | 530/350 |

OTHER PUBLICATIONS

Olivera et al., Science, vol. 230, (1985) pp. 1338–1343.
Gray et al., Ann. Rev. Biochem., 57 pp. 655–700 (1988).
Ahmad, S. et al., *Brain Research*, 453:247–256 (1988).
Anderson, A. J., et al., *Neuroscience Letts.*, 82:177–180 (1987).
Bennett, J. P. et al., *Neurotransmitter Receptor Binding*, pp. 61–89, Raven Press, N.Y. (1983).
Chou, P. Y., Fasman, G. D. *Biophysics J.*, 26, pp. 367–384 (1979).
Gray, W. R., et al., *Ann. Rev. Biochem.*, 57, pp. 655–700 (1988).
Haley, T., et al., *Brit. J. Pharmacol.*, 23, pp. 12–15 (1957).
Kessler, H., et al., *Angew. Chim. Int. Eng. Ed.*, 27, pp. 490–536 (1988).
Kirino, T., *Brain Research*, 239, pp. 57–69 (1982).
McCleskey, E. W., et al. *PNAS*, 84, pp. 4327–4331 (1987).
Morel, N., Meunier, F-M., *J. Neurochem.*, 36, pp. 1766–1773 (1981).
Olivera, B., et al., *Science*, 230, pp. 1338–1343 (1985).
Pulsinelli, W. A., et al., *Stroke*, 10, pp. 267–272 (1979).
Sano, K., et al., *Eur. J. Pharmacol.*, 141, pp. 235–141 (1987).
Schweitzer, E., *J. Neurosci.*, 7, pp. 2948–2956 (1987).
Tsien, R. W., et al., *TINS*, 11, pp. 431–438 (1988).
Van Reempts, J., et al., *Acad. Anaesthesiolica Belge*, 35, Suppl., pp. 209–218 (1984).
Wauquier, A. et al., *Neuroscience and Biobehavioral Reviews*, 11 pp. 287–306 (1987).
Yamaguchi, T., Klatzo, I., in *Cerebral Ishemia*, (Bes, A., Braquet, P., and Sisejo, B. K. eds.), Elsevier Sciences Publ., pp. 13–24 (1984).
Yamashiro, D., *Int. J. Protein Peptide Res.*, 30, pp. 9–12 (1987).
Bean, B. P., Annu. Rev. Physiol. 51:367–84 (1989).
Choi, D. W., "Calcium-Mediated Neurotoxicity: Relationship to Specific Channel Types and Role in Ischemic Damage".
Greenberg, D. A., Curr. Neurol. 6:91–121 (1986).
Hossmann, K. -A, "Calcium Antagonists for the Treatment of Brain Ischemia: A Critical Appraisal".
Marqueze, Beatrice, et al., Molecular Pharmacology, 34:87–90.
Tateishi, A., et al., Stroke 20:1044–1050 (1989).
Vibulsreth, S., et al., "Failure of Nimodipine to Prevent Ischemic Neuronal Damage in Rats.".

*Primary Examiner*—Lester L. Lee
*Assistant Examiner*—Avis M. Davenport
*Attorney, Agent, or Firm*—Peter J. Dehlinger

[57] ABSTRACT

A method of reducing neuronal damage related to an ischemic condition in a human patient, such as stroke-induced damage, by administration of a binding/inhibitory omega-conotoxin peptide.

17 Claims, 11 Drawing Sheets

```
SERIES G 1         5         10        15        20        25        30

  GVIA   C K S X G S S C S X T S Y N C C R - S C N X Y T - K R C - - Y*

  TVIA   C L S X G S S C S X T S Y N C C ...(C-Terminal region not yet
                                                          sequenced)

  GVIIA  C K S X G T X C S R G M R D C C T - S C L L Y S N K - C R R Y

  RVIA   C K P X G S X C R V S S Y N C C S - S C K S Y N - K K C G

  SVIA   C R S S G S X C G V T S I - C C - G R C - - Y R G K - C T
  (neg predictor)


SERIES M

  Snew   C K L K G Q S C R K T S Y D C C S G S C G R - S G K - C

  MVIIA  C K G K G A K C S R L M Y D C C T G S C - R - S G K - C*

  MVIIB  C K G K G A S C H R T S Y D C C T G S C N R - - G K - C*
```

SERIES G 1 5 10 15 20 25 30

GVIA C K S X G S S C S X T S Y N C C R - S C N X Y T - K R C - - Y*

TVIA C L S X G S S C S X T S Y N C C ...(C-Terminal region not yet sequenced)

GVIIA C K S X G T X C S R G M R D C C T - S C L L Y S N K - C R R Y

RVIA C K P X G S X C R V S S Y N C C S - S C K S Y N - K K C G

SVIA (neg predictor) C R S S G S X C G V T S I - C C - G R C - - Y R G K - C T

SERIES M $S_{new}$ C K L K G Q S C R K T S Y D C C S G S C G R - S G K - C

MVIIA C K G K G A K C S R L M Y D C C T G S C - R - S G K - C*

MVIIB C K G K G A S C H R T S Y D C C T G S C N R - - G K - C*

Fig. 1

X = Hyp

METHOD OF TREATING ISCHEMIA-RELATED NEURONAL DAMAGE

FIELD OF THE INVENTION

The present invention relates to a method of reducing neuronal damage associated with an ischemic condition, such as stroke.

REFERENCES

Ahmad, S. and Miljanich, G., Br. Res. 453:247-256 (1988). Anderson, A. and Harvey, A., Neurcsci. Lett. 82:177-180 (1987).

Bennett, J. P. and Yamamura, H. I., Neurotransmitter Receptor Binding, pp. 61-89, Raven Press, N.Y. (1983).

Chou, P. Y. and Fasman, G. D., Biophys. J., Vol. 26, pp. 367-384.

Gray, W., Olivera, B., and Cruz, L. (1988), Annual Review of Biochemistry 57:665-700.

Haley, T. and McCormich, W., Brit. J. Pharmacol. 12:12-15 (1957).

Kessler, H., Gehrke, M., and Griesinger, C., *Angew. Chem. Int. Ed.*, Vol. 27 (1988) pp. 490-536.

Kirino, T., *Brain Res.* 239:57-69 (1982).

McCleskey, E., Fox, A., Feldman, D., Cruz, L., Olivera, B., Tsien, R., Yoshikami, D., *Proc. Natl. Acad. Sci.* (USA) 84:4327-4331 (1987).

Morel, N. and Meunier, F. -M., J. Neurochem. 36:1766-1773 (1981).

Olivera, B., Gray, W., Zeikus, R., McIntosh, J., Varga, J., Rivier, J., de Santos, V., Cruz, L. J., *Science* 230: 1338-1343 (1985).

Pulsinelli, W. and Brierley, J., Stroke 10:267-272 (1979).

Sano, K., Enomoto, K., Maeno, T., Eur. J. Pharmacol. 141:235-241 (1987).

Schwartz, R. M. and Dayhoff, M. O. (1978), *Atlas of Protein Sequence and Structure*, 5 suppl. 3:353-358, Nat. Biomed. Res. Found., Washington, D.C.

Schweitzer, E., J. Neurosci. 7:2948-2956 (1987)

Tsien, R., Lipscombe, D., Madison, D., Bley, K., Fox, A., TINS 11:431-438.

Van Reempts, J. and Borgers, M. (1984), Acad. Anaesthesiolica Belge 35, Supplement, 209-218.

Wauquier, A., Edmonds, H., Clincke, G. (1987), Neuroscience and Biobehavioral Reviews 11:287-306.

Yamaguchi, T. and Klatzö, I., *in Cerebral Ischemia* (Bes, A., Braquet, P., and Siesjo, B. K., eds), Elsevier Sciencer Publ., pp 13-24 (1984).

Yamashiro, D., *Int. J. Peptide Protein Res.*, 30:9-12 (1987).

BACKGROUND OF THE INVENTION

Ischemic damage to the central nervous system (CNS) may result from either global or focal ischemic conditions. Global ischemia occurs under conditions in which blood flow to the entire brain ceases for a period of time, such as may result from cardiac arrest. Focal ischemia occurs under conditions in which a portion of the brain is deprived of its normal blood supply, such as may result from occlusion of a cerebral vessel, traumatic head injury, edema, and brain tumors.

Both global and focal ischemic conditions have the potential for producing widespread neuronal damage, even if the ischemic condition is transient. Although some permanent neuronal injury may occur in the initial minutes following cessation of blood flow to the brain, most of the damage in global and focal ischemia occurs over hours or more typically days following the ischemic onset. Much of this neuronal damage is attributed to secondary consequences of reperfusion of the tissue, such as the release of vasoactive products by damaged endothelium, and the release of cytotoxic products (free radicals, leukotrienes, etc.) by damaged tissues.

Several drug strategies have been proposed for treatment of stroke and other neuronal conditions related to ischemia, and these have been reviewed in recent articles (e.g., Wauquier). Anti-coagulants, such as heparin, have been examined, but with mixed results. Similarly, antivasoconstriction agents, such as flunarazine, excitatory neurotransmitter antagonists, such as MK-801 and AP7, and anti-edemic compounds have shown mixed results, with no clear benefits to outweigh a variety of side effects, including neurotoxicity or increased susceptibility to infection.

Two general classes of vasodilators have been studied for possible treatment of neuronal ischemic damage. Non-specific vasodilators, including papaverine, prostacyclin, pentoxifylline, and nitroprusside failed to demonstrate any clear benefit in reducing ischemic damage. A second general class of vasodilators includes a variety of calcium-antagonist vasodilator drugs. Verapamil and related compounds which prevent calcium entry into smooth and striated muscles appear to be effective only at high drug concentrations, where serious cardiotoxicity effects may ensue. Dihydropyridines, such as nimodipine, produced mixed results—some neurological improvement may be seen, but increased cerebral edema has also been observed. Benzothiazepines, as exemplified by diltiazem, have shown moderate protective effects, but these drugs also appear to cause undesired side effects such as hypotension which may be inimical to treatment.

In summary, drugs which have been proposed to date for the treatment of stroke and other ischemic-related conditions of the brain are either (i) relatively ineffective, (ii) effective only at dosage levels where undesired side effects are observed, and/or (iii) produce systemic effects, such as hypotension, which compromise the potential effectiveness of the drug.

SUMMARY OF THE INVENTION

It is therefore a general object of the invention to provide an effective drug treatment for stroke and other ischemia-related brain conditions.

It is still another object to provide novel peptide compounds for use in the treatment method.

In one aspect, the invention includes a method of reducing neuronal damage related to an ischemic condition in a human patient by administering to the patient a pharmacologically effective amount of a binding/inhibitory omega-conotoxin (OCT) peptide.

Treatment with the peptide is effective to significantly reduce (a) anatomical damage in the brain, as evidenced by reduced damage to hippocampal CA1 cells, and (b) loss of brain function, as evidenced by reduced loss of short-term memory.

The binding/inhibitory conotoxin is characterized by one or some of the following properties:

(a) specific binding to OCT binding sites associated with calcium channels in neuronal-cell membranes, as evidenced by competitive inhibition of OCT peptide binding to electric-ray electric-organ synaptosomes, or rat brain synaptosomes;

(b) inhibition of voltage-gated calcium currents selectively in neuronal tissue, as evidenced by inhibition of voltage gated calcium currents in cultured mouse neuroblastoma cells, but not voltage-gated calcium currents in muscle cells, such as dissociated guinea pig cardiac ventricular cells; and (c) inhibition of neurotransmitter release selectively in neuronal tissue, as evidenced by inhibition of induced ATP release from electric ray electric organ synaptosomes, but not blockade of evoked neurotransmitter release at a mammalian neuromuscular junction of skeletal muscle.

OCT peptides effective in the treatment method may be further characterized by their ability to induce shaking in mice following intracerebral injection.

The binding/inhibitory OCT peptide may be a G-group peptide, such as GVIA, GVIIA and RVIA peptide, including binding/inhibitory analogs thereof, or an M-group peptide such as SVIB, MVIIA, MVIIB peptide, including binding/inhibitory analogs thereof. The isoelectric point of the peptide is preferably between about 10.5-12.0.

The three-dimensional structures of preferred M-group peptides are further characterized by the following NMR-NOE based interatomic distances of about 4.5 angstroms (long-range) or 2.5 angstrom (short-range) between protons of the designated amino acid residue amide nitrogen found in OCT MVIIA, or as otherwise specified:

Long-range:
Lys (position 2) and Cys (position 16)
Gly (position 5) and Cys (position 28)
Lys (position 26) and Cys (position 20)
alpha H Cys (position 28) and Gly (position 18)
beta H Cys (position 28) and Lys (position 2)
alpha H Lys (position 26) and Cys (position 8)
beta H Cys (position 1) and Cys (position 16)
beta H Cys (position 28) and Gly (position 5)
beta H Cys (position 28) and Gly (position 18)
Short-range:
Ser (position 24) and Gly (position 25)
Asp (position 14) and Cys (position 15)
Tyr (position 13) and Asp (position 14)
Gly (position 25) and Lys (position 26)

The three-dimensional structures of preferred G-group peptides are characterized by peptide backbones having similar three-dimensional conformations as that of OCT MVIIA as defined by the above NMR-NOE constraints.

These and other objects and features of the invention will become more fully apparent when the following detailed description of the invention is read in conjunction with the accompanying drawings.

BRIEF DESCRIPTION OF THE DRAWINGS

FIG. 1 shows primary sequences of OCT peptides, arranged in G and M groups of OCT peptides;

DETAILED DESCRIPTION OF THE INVENTION

I. Preparation of OCT Peptides

Omega-conotoxin (OCT) peptides are peptide toxins produced by marine snails of the genus Conus, and which act as calcium channel blockers (Gray). About 300 species of cone snails in the Conus genus have been identified, and a variety of OCTs from several of these species have been isolated. The primary sequences of seven OCT peptides of the eleven which have been completely sequenced are shown in FIG. 1. Conventional letter initials are used for the amino acid residues, and X represents 4-hydroxyproline, also abbreviated 4Hyp. Known C-terminal amidation is indicated by a "*" in FIG. 1. The peptides have been grouped into M- and G-group peptides, as described in Section IV below.

The identifying names of the peptides are also given in the figure, and these names will be used herein to refer to the specific OCT peptide. For example, the peptide whose sequence is designated MVIIA will be referred to herein as OCT MVIIA peptide, or simply MVIIA peptide. The MVIIA and GVIA peptides also have the common names CmTx and CgTx, respectively.

Figure 2:
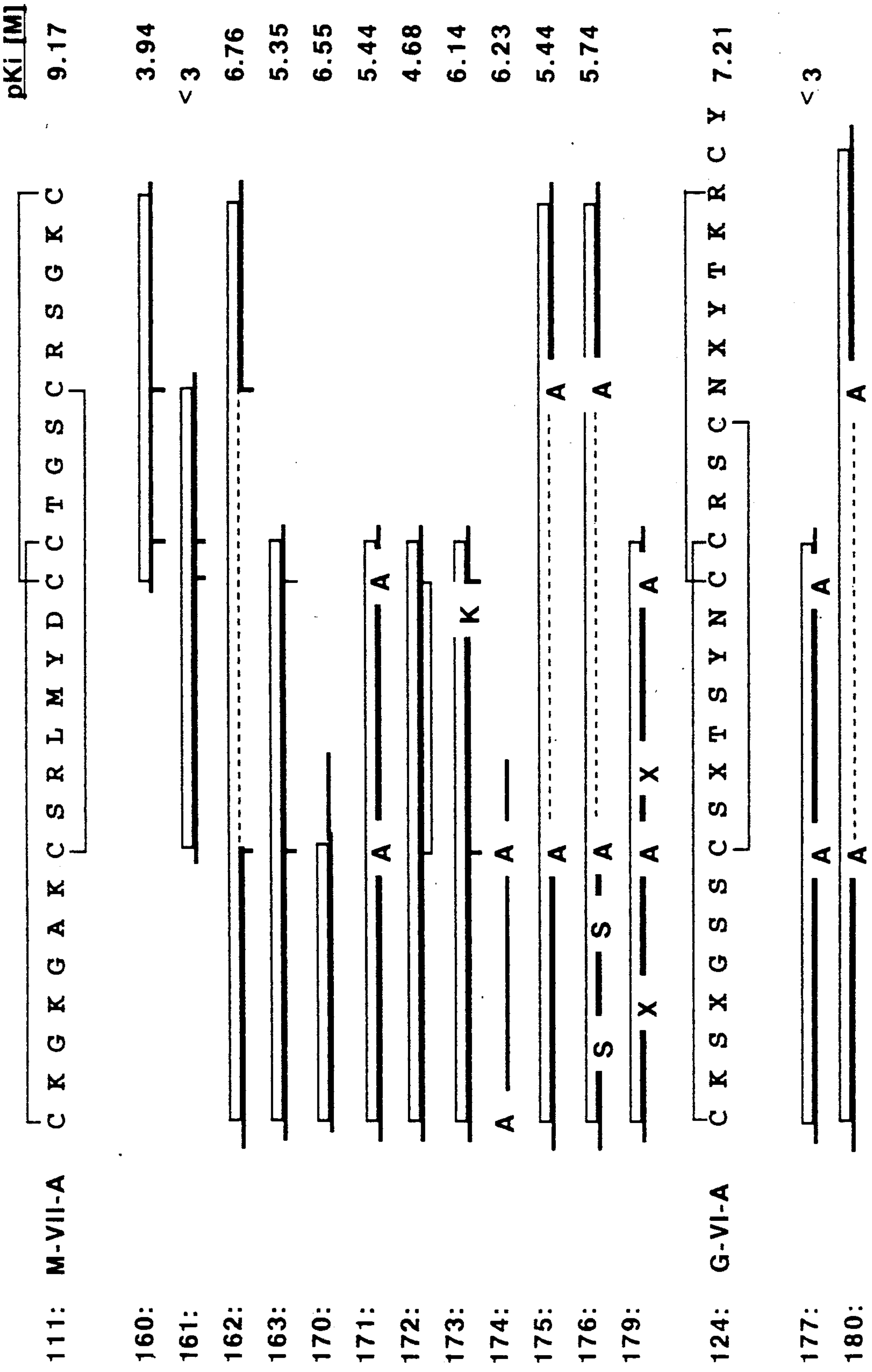
FIG. 2 shows OCT peptide fragments used in binding studies carried out in support of the present invention.

The MVIIA and GVIA peptides are also shown in FIG. 2, along with their three disulfide linkages, as demonstrated chemically or spectroscopically. All of the OCT peptides in FIG. 1 have these three linkages between the first and fourth, second and fifth, and third and sixth cysteine (Cys) residues.

OCT peptides, including the MVIIA, MVIIB, GVIA, GVIIA, RVIA, SVIA and SVIB peptides shown in FIG. 1, and binding/inhibitory analogs thereof, can be synthesized by solid phase synthesis, according to the methods detailed in Examples 1 and 2.

Briefly, N-alpha-protected amino acid anhydrides are prepared in crystallized form and used for successive amino acid addition to the N-terminus. At each residue addition, the growing peptide (on a solid support) is acid treated to remove the N-alpha-protective group, washed several times to remove residual acid and to promote accessibility of the peptide terminus to the reaction medium. The peptide is then reacted with an activated N-protected amino acid symmetrical anhydride, and the solid support is washed. At each residue-addition step, the amino acid addition reaction may be repeated for a total of two or three separate addition reactions, to increase the percent of growing peptide molecules which are reacted. Typically, 1-2 reaction cycles are used for the first twelve residue additions, and 2-3 reaction cycles for the remaining residues.

After completing the growing peptide chains, the protected peptide resin is treated with liquid hydrofluoric acid to deblock and release the peptides from the support. For preparing an amidated peptide, the resin support used in the synthesis is selected to supply a C-terminal amine, after peptide cleavage from the ring.

The three disulfide linkages in the peptides may be formed by air oxidation in the presence of dithiothreitol (DTT) at room temperature or at 4° C. over an extended reaction period. Alternatively, where the correct or desired bridging cannot be achieved by random oxidation, a chemically directed process may be used in which the bridges are formed sequentially, one bridge at a time. The following side-chain protecting groups could be used for each pair of cysteine residues: 4-methylbenzyl, ethylcarbamoyl, and acetamidomethyl. These protecting groups constitute an orthogonal set in which any one kind of protecting group can be removed under conditions that do not affect the other two.

The strategy here involves removing one kind of protecting group from a pair of cysteine residues, followed by oxidation to form the first disulfide bridge. A second kind of protecting group is then removed, again followed by oxidation to form the second bridge. A third bridge, if needed, is formed in like manner. An example is the synthesis of compound (FIG. 2) No. 163 (with a bridge linking positions 1 and 16) followed by conversion to compound 172 (with the second bridge linking positions 8 and 15).

The peptide can be isolated by an initial separation by gel filtration, to remove peptide dimers and higher polymers, and also to remove undesired salts, such as guanidine hydrochloride, used in the oxidation reaction. The partially purified peptide is further purified by preparative HPLC chromatography, and the purity of the peptide confirmed by amino acid composition analysis. Details of the preparation and purification of the MVIIA peptide are given in Example 1. The same methods are applied in Example 2 for preparation and purification of the MVIIB, GVIA, GVIIA, RVIA, SVIA, and SVIB peptides.

FIG. 2 shows portions of MVIIA and GVIA peptides which were also prepared for peptide fragment binding studies, described in Section IV. The heavy lines in the figure indicate the portion of the corresponding MVIIA or GVIA peptide which was synthesized, and the light-line loop, the disulfide linking which was formed in the peptides. A small arrow above a Cys position indicates that the Cys residue is blocked (with an acetamidomethyl group) and therefore unable to participate in disulfide bridging. Thus for example, the peptide fragment labeled 160 extends between the third and sixth Cys residues corresponding to the C terminus of the full-length MVIIA peptide, and has a disulfide bridge between the third and sixth Cys, the fourth and fifth Cys residues being blocked. The peptide fragment labeled 162 includes a deletion between the positions 9 and 19, and is linked between the first and sixth Cys residues, the second and fifth Cys residues being blocked. The A, S, and X designations in the figure indicate Ala, Ser, and 4Hyp substitutions, respectively, at the positions shown.

The peptide fragments shown in FIG. 2 were prepared substantially as described in Example 3, following the method detailed in Example 1, but using a single-coupling protocol. All of the peptide fragments are amidated at the C-terminal residues.

II. Binding/Inhibitory OCTs

This section describes in vitro binding and inhibitory properties of OCT peptides which are effective in the treatment method of the invention. According to one aspect of the invention, the in vitro properties are used as indicators selecting and identifying natural and analog conotoxin peptides which are effective in the treatment method of the invention. More generally, it has been discovered that (a) conotoxin peptides can be characterized as binding/inhibitory, according to selected in vitro binding and/or inhibitory properties, and (b) binding/inhibitory peptides are effective in reducing neuronal damage in ischemia-related neuronal conditions.

As defined herein, binding/inhibitory OCT peptides have at least one of the following binding/inhibitory activities:

(a) Specific, high-affinity binding to OCT binding sites associated with calcium channels in neuronal-cell membranes, as evidenced by competitive inhibition of OCT binding to rat brain synaptosomes or to electric-ray electric-organ (fish) synaptosomes;

(b) inhibition of voltage-gated calcium currents selectively in neuronal tissue, as evidenced by inhibition of voltage-gated calcium currents in cultured mouse neuroblastoma N1E-115 cells, but not in muscle cells, such as dissociated guinea pig cardiac ventricular cells; and (c) inhibition of neurotransmitter release selectively in neuronal tissue, as evidenced by inhibition of ATP release from fish synaptosomes, but not neurotransmitter release such as mammalian neuromuscular junction of skeletal muscle, such as mouse diaphragm neuromuscular junction.

A. Specific, High Affinity Binding to OCT Receptors

High-affinity binding to OCT sites in neuronal tissue can be demonstrated with a variety of cell types and synaptosomal cell fractions. Example 4 describes the determination of OCT binding constants, based on competitive displacement of MVIIA peptide from electric-ray electric-organ synaptosomal membranes, also referred to herein as fish synaptosomes.

Fish electric organ synaptosomes are prepared by the gradient centrifugation method detailed in Example 4. The binding constant $K_d$ of the MVIIA peptide for the synaptosomes is determined by a saturation binding method in which increasing quantities of radiolabeled peptide are added to the synaptosomes, and the amount of labeled material bound at each concentration is determined. The plot of bound peptide as a function of concentration is then used to calculate a $B_{max}$, the concentration of binding sites on the synaptosomes, and $K_d$ following standard methods. The $K_d$ value obtained for the MVIIA peptide is about 0.4 nM, as seen in Table 3 of Example 4. The corresponding $pK_i$ value is 9.4.

Figure 3:
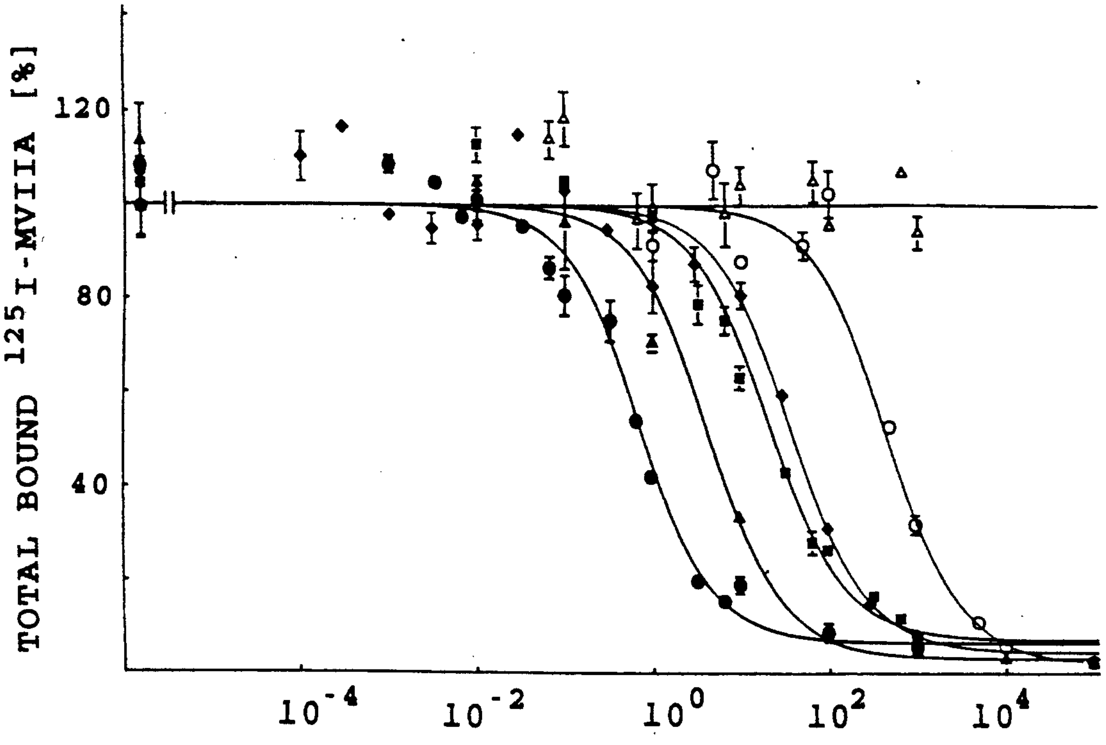
FIG. 3 shows computer-fit competitive binding curves for OCT peptide binding to fish electric organ synaptosomes; MVIIA (solid circles), GVIIA (solid triangles), MVIIB (solid squares), GVIA (solid diamonds), RVIA (open circles), and SVIA (open triangles)

Competitive binding assays, to determine $K_i$ binding constants for other OCT peptides, are carried out by addition of test peptides, over a concentration range between about $10^{-3}$ and $10^{-13}$M peptide, to fish synaptosomes having bound, labeled MVIIA peptide. The synaptosome material is then rapidly filtered, washed and assayed for bound radiolabel. The binding constant, $K_i$, of the test peptide can be determined using computer-fit competitive binding curves, such as shown in FIG. 3 for GVIA peptide, with the results shown in Table 3 of Example 4. Of the six peptides examined (in addition to MVIIA), five show high-affinity binding, as judged by a $pK_i$ greater than 6. One of the peptides, SVIA, shows relatively low affinity binding and thus fails to meet the criteria of binding/inhibitory OCT peptides.

Table 3 in Example 3 also gives approximate $K_i$ and $pK_i$ values for a number of OCT MVIIA and GVIA peptides fragments shown in FIG. 1. The significance of the fragment binding constants will be discussed below in Section IV.

Figure 4:
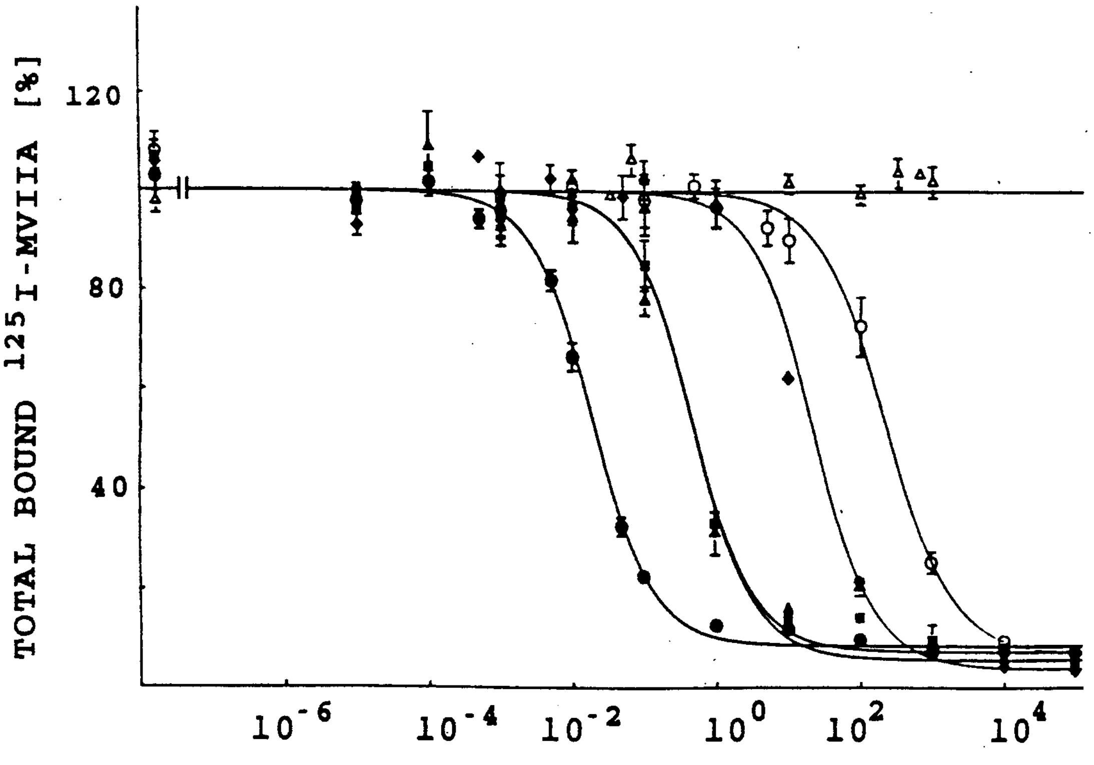
FIG. 4 shows shows computer-fit competitive binding curves for OCT peptide binding to rat brain synaptosomes; MVIIA (solid circles), MVIIB (solid triangles), GVIA (solid squares), GVIIA (solid diamonds), RVIA (open circles), and SVIA (open triangles)

Similar competitive binding studies can be carried out with mammalian synaptosome preparations, such as the rat brain synaptosome preparation described in Example 5. An analysis of the competitive binding curves, such as shown in FIG. 4 for the MVIIA peptide, obtained in studies with the rat brain preparation indicates a single binding site for OCTs, with the corresponding $IC_{50}$ values (that concentration of competing compound at which specific binding is inhibited by 50%) shown in Table 4 in Example 5.

Studies reported in Example 6 further indicate that OCT peptide binding activity can be assessed with respect to several cultured neuronal cells. The different cell types and strains which were employed are shown at the left in Table 5 in this example, along with the corresponding concentration of specific binding sites measured by the addition of 1 nM labeled MVIIA peptide to the cells. Two of the neuroblastoma cell strains, IMR-32 and SY5Y(+RA), show relatively high concentrations of OCT surface binding sites.

In summary, both synaptosome preparations and cultured neuronal cells are suitable for testing binding affinity of test OCT peptides. One preferred system is electric-ray electric organ synaptosomes, where specific, high-affinity binding is evidenced by a $pK_i$ of 6 or greater, as determined by competitive displacement of MVIIA peptide.

B. Inhibition of voltage-gated calcium currents

Voltage-gated calcium channels are present in neurons, and in cardiac, smooth, and skeletal muscle and other excitable cells, and are known to play a variety of roles in membrane excitability, muscle contraction, and cell secretion, such as in synaptic transmission (McCleskey). In neuronal cells, voltage-gated calcium channels have been classified into L, T, and N channels, each with characteristic gating voltage, inactivation rate, and selective modulation by neurochemicals (Tsien).

GVIA OCT has been reported to block voltage-gated calcium channels in a variety of neuronal cells, including dorsal root ganglion (DRG) neurons (McCleskey). This blockage or inhibition of calcium channel currents has been reported to be neuron-specific, since calcium current inhbition by the peptide was not observed in cardiac, smooth, and skeletal muscles.

One suitable system for testing inhibition (blockage) of neuronal calcium channels is the mouse neuroblastoma cell line, strain N1E115. Membrane currents are conveniently measured with the whole cell configuration of the patch clamp method, according to the procedure detailed in Example 7. Briefly, a voltage clamp protocol was performed in which the cell potential was stepped from the holding potential of about −100 mV to test potentials that ranged from −60 mV to +20 mV, and the cell was held at the holding potential for 5 seconds between pulses.

Figure 5B:
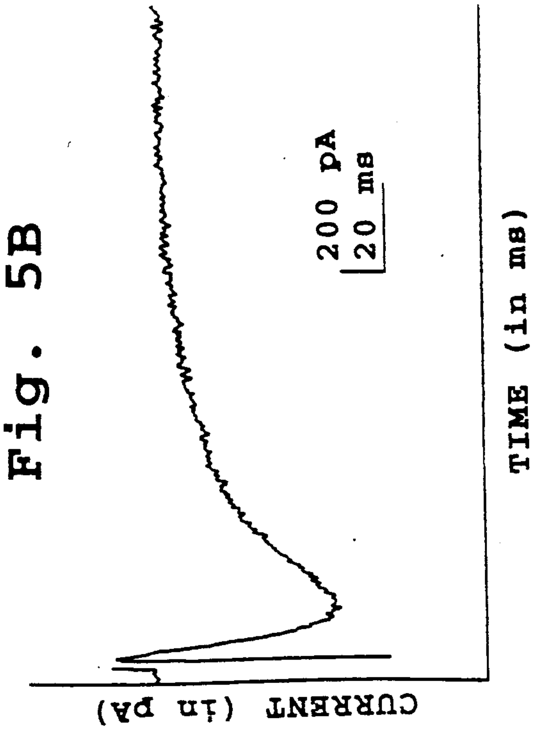
FIGS. 5A-5D show voltage-gated calcium current traces induced by a voltage step from −100 or −80 mV to −20 mV in untreated neuroblastoma cells (5A) and in neuroblastoma cells exposed to increasing concentrations of OCT peptide MVIIA (5B-5D)
Figure 5D:
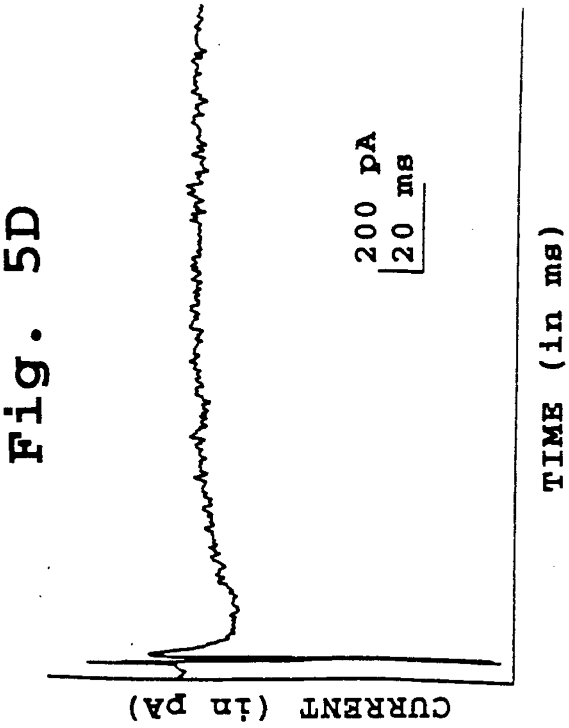
Figure 5A:
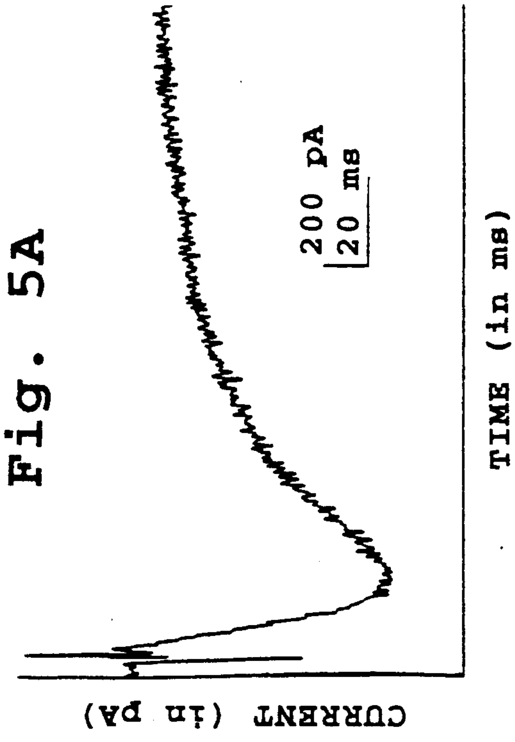

FIG. 5A shows a typical inward calcium current elicited by a voltage step from −100 mV to −20 mV in the absence of OCT. In this, and most of the recordings, Ba replaced Ca as the charge-carrier through the calcium channels in order to increase the signal (Tsien). According to the procedure described in Example 7, an N1E115 neuroblastoma cell was bathed in saline with sodium replaced by N-methyl-D-glucamine (NMDG), and 10 mM Ba instead of 2 mM Ca. These substitutions reduced the sodium current that would otherwise have contaminated the calcium-current record, and increased the calcium current above what it would have been with only 2 mM Ca in the bath. Potassium currents were blocked by TEA in the bath and Cs in the pipet solution.

As seen from FIG. 5A, the calcium current activates quickly (within about 20 ms) and inactivates with a time constant of 30 to 40 ms. The calcium current is measured by the amplitude of the peak inward current elicited by the depolarization peak, and has a measured value of about −1196 pA. The cell in FIG. 5A was also exposed to 1 μM nifedipine, a dihydropyridine, which is expected to effectively block L-type calcium channels in the neuroblastoma cells. The calcium current observed is thus expected to be predominantly an N-type calcium channel current.

Figure 5C:
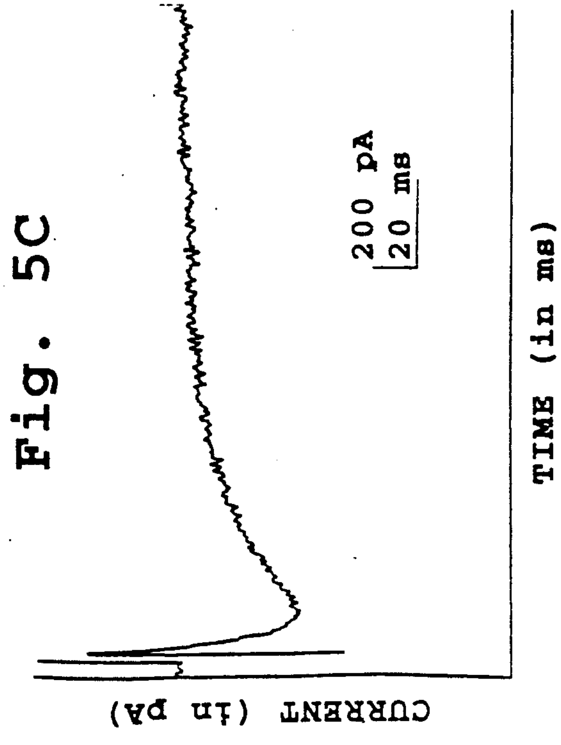

FIG. 5B shows the effect on the calcium current when an $N_{IE}$115 cell was exposed to a solution containing 10 nM MVIIA peptide. The measured current amplitude in the same cell as shown in FIG. 5A (same scale) was reduced to about −857 pA. With increasing concentrations of OCT peptide, the measured calcium current dropped to −534 pA, at 50 nM OCT peptide, and to −257 pA, at 200 nM OCT peptide, as seen in FIGS. 5C and D, respectively.

The $ED_{50}$ concentration, at which 50% inhibition of calcium current is produced, is determined from the voltage-gated current amplitudes, plotted as a function cf OCT peptide concentration.

Figure 6:
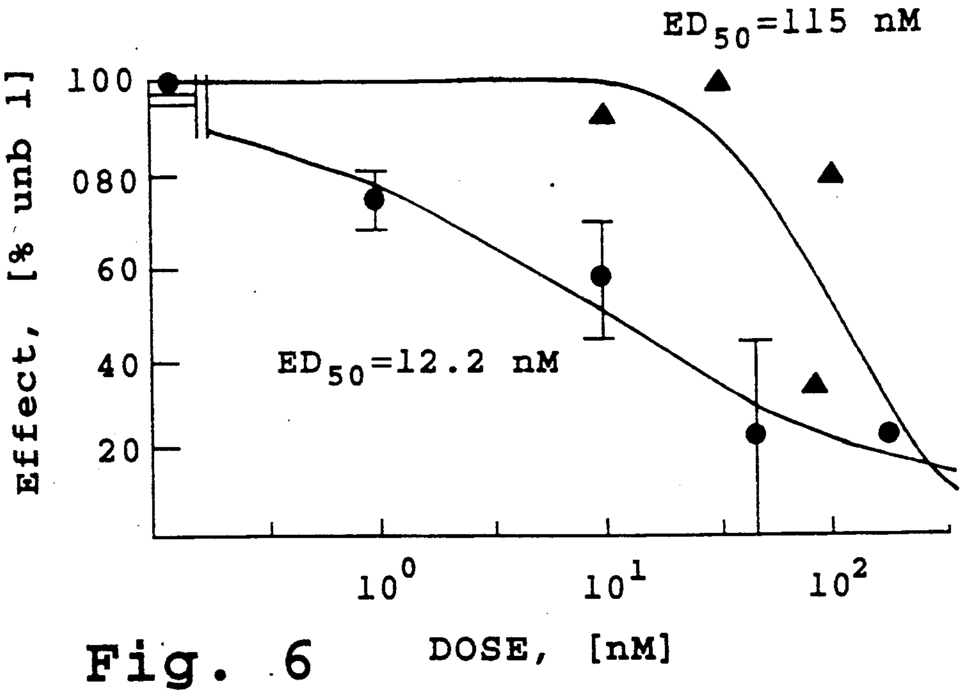
FIG. 6 plots the percent inhibition of peak inward calcium currents in neuroblastoma cells as a function of MVIIA (solid triangles) and GVIA (solid circles ) OCT.

The responses of voltage-gated calcium current to increasing dosages of OCTs MVIIA and GVIA are shown in FIG. 6. The calculated $ED_{50}$ is 12 nM for GVIA and 115 nM for MVIIA, indicative of high inhibitory peptide activity. The $ED_{50}$ concentration for test OCT peptides can be readily determined in a like manner. Test peptides which have $ED_{50}$ values of less than about 1 μM and preferably less than about 200 −250 nM (Table 4, Example 5) in the above neuroblastoma system are classed as having the requisite calcium current inhibitory activity.

Test peptides which are inhibitory for neuronal cell calcium currents can be further tested in non-neuronal cells, to confirm that the peptide activity in blocking calcium currents is specific to neuronal cells. A variety of muscle cell types which are refractory to calcium-current inhibition by OCTs, such as vertebrate embryo heart and skeletal muscle cells, are suitable (McCleskey). Cell current measurements are made substantially as outlined above and detailed in Example 7.

C. Selective Inhibition of Neurotransmitter Release

A third property of binding/inhibitory OCT peptides is the ability to specifically inhibit neurotransmitter release in neuronal cells, but not at a mammalian neuromuscular junction of a skeletal muscle. This property may be related to (a) specific binding of active peptide to the neuronal cell membrane and (b) resultant inhibition of calcium currents produced by such binding, and thus may represent a consequence of the binding and current-inhibition properties of OCT peptides.

In one standard method for measuring neurotransmitter release, ATP release from synaptosomes, such as fish synaptosomes is assayed. Here, the synaptosomes are suspended in medium containing luciferase, and scintillation events are counted after exocytotic release of ATP from the synaptosomes. In the procedure detailed in Example 8, synaptosomal release of ATP is evoked by injecting potassium at a high concentration into the medium, producing voltage-gated calcium currents which are accompanied by the concommitant release of ATP and acetylcholine..

Test peptides are included in the synaptosome medium at several concentrations between about 1 and 1000 nM, and the reduction in ATP levels is measured before and after peptide addition. From a plot of ATP release inhibition as a function of peptide concentration, the $IC_{50}$ value, at which 50% ATP release inhibtion occurs, is determined. Table 6 in Example 8 gives the $IC_{50}$ values determined for the MVIIA and GVIA active peptides.

The test OCT peptide may also be assayed for non-inhibition of neuromuscular transmission at a mammalian neuromuscular junction of skeletal muscle. Various model systems for measuring the effect of test compounds on neurotransmitter release at a neuromuscular junction have been described (Sano; Anderson). In both an isolated mouse diaphragm system described by Sano, and a mouse triangularis sterni system described by Anderson, OCT MVIIA was reported to show little or no inhibitory efects.

D. Mouse Shaker Test

Peptides which are can be classed as binding/inhibitory peptides in the in vitro binding and inhibition activity tests described above can be further tested for activity in an in vivo mouse shaker model system. This test system is modeled on an earlier reported finding that intracerebroventricular (ICV) administration of MVIIA peptide in mice produces whole-body tremors (Olivera).

In the shaker test, unanesthetized animals are given a selected dose of the test peptide by intracerebral administration. Animals which show spontaneous tremors within about 30 minutes after peptide administration are scored as positives. Table 7 in Example 9 shows the shaker results obtained on tests with increasing doses of OCT's MVIIA, GVIA, and SVIA. The middle column shows the number of animals which were tested at each dose, and the right column, the percent number of "shakers", i.e., animals showing shaking behavior. The MVIIA and GVIA OCT peptides, which are both active as judged by the binding and inhibition criteria described above, give a dose-dependent shaker response, with both peptides showing a high percentage of shakers at 0.3 μg dose. By contrast, the SVIA peptide, which is inactive by the above binding activity criterion, gives only a low percentage of shakers, even at a dose of 10 μg.

The shaker model data above demonstrate that the mouse shaker model may provide a reliable in vivo test of OCT peptide activity, i.e., the model provides a useful predictor of OCT activity in the treatment method of the invention. The shaker model may also be useful in determining effective treatment dose ranges of a test OCT peptide. As will be seen in Section III below, dose ranges effective for stroke treatment are roughly comparable to the doses at which a low-to-moderate percentage of shakers are observed. The shaker model system can also be used to test toxicity effects at projected treatment doses.

III. Treatment Method

The present invention provides a treatment method for reducing neuronal damage related to an ischemic condition in a human patient. The ischemic conditions may be due to an interruption in cerebral circulation, such as caused by cardiac failure, or other condition leading to global loss of blood supply to the brain, or to localized interruptions in blood flood, such as due to cerebral hemorrhaging, or localized thrombotic or embolic events, or head trauma.

The ischemic condition to be treated is generally associated with stroke, defined as the sudden diminution or loss of neurological function caused by an obstruction or rupture of blood vessels in the brain. In stroke, as well as in other types of cerebral ischemic conditions, the peptide treatment is aimed at preventing or reducing secondary brain damage resulting from the original ischemic event. The secondary damage typically includes cerebral cell destruction, or lesions, in the area surrounding the ischemic injury, in the case of focal ischemia, and also in areas of selective vulnerability in lesions, such as the hippocampus or basal ganglia, in the case of global ischemia. The secondary damage may often be manifested by functional impairment, such as loss of short-term or long-term memory. As will be seen below, the treatment method of the invention is effective in reducing or preventing both anatomical and functional secondary damage related to ischemia.

The OCT peptide administered in the treatment method is a binding/inhibitory OCT peptide as defined in Section II above, including the MVIIA, MVIIB, GVIA, SVIB, GVIIA, and RVIA OCT peptides and binding/inhibitory analogs of natural OCT peptides having amino acid substitutions selected according to the constraints discussed in Section IV.

The peptide is formulated for parenteral administration in a suitable inert carrier, such as a sterile physiological saline solution. The concentration of peptide in the carrier solution is typically between about 0.1–10 mg/ml. The dose administered will be determined by route of administration. One suitable route is intracerebroventricular (ICV), at a dose level of about 0.1–50 μg peptide/kg body weight, depending on the binding and inhibitory values of the peptide. A pharmaceutically effective dose, i.e., a dose effective to produce significant reduction in anatomical and/or functional damage, can be estimated, as noted above, from the dose response seen in the mouse shaker model. The dose level can also be estimated, for new OCT peptides, by comparison with established effective doses for known peptides, corrected for observed differences in in vitro binding and inhibitory activities.

As reported below, and according to an important feature of the invention, it has been found that there is little or no loss of protective effect of the peptide when administered well after the ischemic effect, e.g., one hour following the period of transient occlusion. The delayed-administration protective effect indicates that the peptide is effective in blocking the events leading from ischemic injury to secondary cerebral injury, since these events may occur over a period of many hours or even days after injury. Thus, the delayed administration may be effective to reduce secondary cerebral damage when administered several hours, or even a day or more, following the onset of ischemia.

The treatment method has been demonstrated in two animal systems which are widely employed as model systems for global ischemia and secondary stroke damage. The first system is the gerbil model of global ischemia produced by transient occlusion of carotid arteries of the neck. For clinical comparisons, the ischemia produced in this model has been likened to that produced by cardiac arrest, since all blood flow to the brain is stopped for a fixed period, typically 5-10 minutes.

Although some differences in particular sequelae have been noted between species, gerbils exhibit the same kind of selective regional damage to ischemia as is found in other mammals, including humans. In particular, the characteristic secondary damage observed in the hippocampal CA1 region is similar to that seen in other mammals, including humans (Kirino; Yamaguchi). Neurons in this area, and especially pyramidal neurons, exhibit a delayed neuronal death over a period of up to 4 days after ischemic injury.

The second model is the rat four-vessel occlusion model. The experimental procedure for producing temporary occlusion produces an ischemia that mimics conditions in the human brain following cardiac arrest, including the following similarities: the ischemic event is temporary, typically 5-30 minutes; it occurs in an unanesthetized state; in most rats the ischemic event is not accompanied by generalized seizures, and animals that have seizures can be excluded from the study. In addition, the occlusion procedure allows the animals to be easily monitored, maintained and analysed.

A. Reduction in Anatomical Damage

Ischemia in the gerbil model system was induced in anesthetized animals by occluding the two carotid arteries for eight minutes, as detailed in Example 10. OCT peptide was administered ICV during the occlusion period, or one hour following occlusion. Four days after occlusion and peptide treatment, the animals were examined histologically for anatomical damage in the hippocampal CA1 region, as detailed in Example 10.

Figure 7A:
FIG. 7A-7B are low-power micrographs of gerbil hippocampus CA1 region in animals after ischemia, and infusion of MVIIA OCT (7A) or drug vehicle (7B)
Figure 7B:
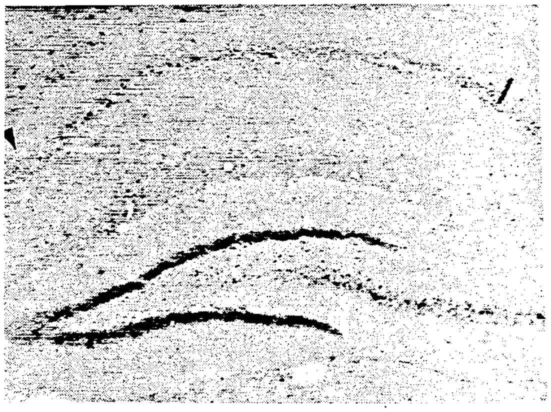
Figure 8A:
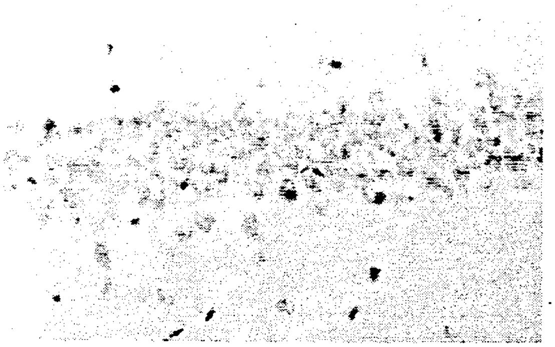
FIGS. 8A-8D are higher power micrographs of cells in the drug-treated ischemic animals (8A, 8C, 8D), in animals receiving vehicle alone (FIG. 8B), in animals showing complete protection by OCT against ischemic cell damage (8C); and in animals showing partial protection by OCT against ischemic cell damage (8D)
Figure 8B:
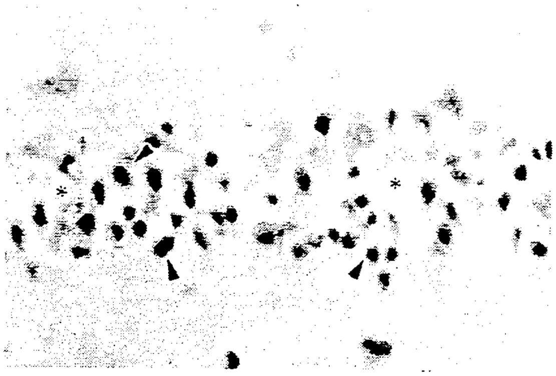
Figure 8C:
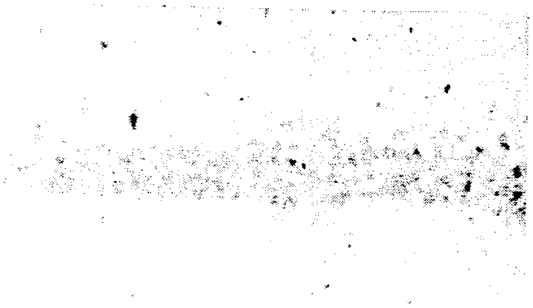
Figure 8D:
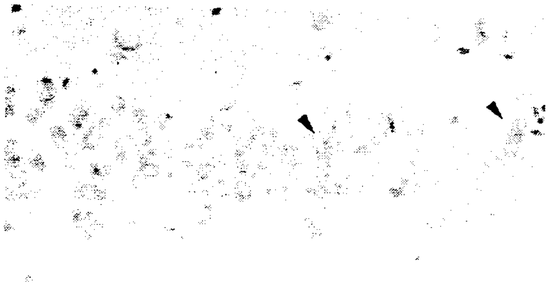

FIGS. 7A and 7B are low-power micrographs of gerbil hippocampus CA1 region in animals after ischemia, and infusion of MVIIA OCT (7A) or drug vehicle (7B). The arrows in the figures indicate the approximate borders of the CA1 region. At higher power, cells in the drug-treated ischemic animals appear normal (FIG. 8A), whereas damage is apparent in the ischemic animals receiving vehicle alone (FIG. 8B). Another example of complete drug protection is seen in FIG. 8C, and an example of partial protection is seen in FIG. 8D, where there are a small number of damaged cells.

Anatomical sections, such as those seen in FIGS. 7 and 8, were scored according to the criteria set out in Example 10. The extent of anatomical damage in ischemic animals treated with MVIIA or GVIA OCT or receiving vehicle alone (control), based on the above scoring system, is given in Table 8 in Example 10. The peptide was administered by ICV infusion during the eight minutes of ischemia, at a total dose indicated in Table 8 in Example 10. As seen, the extent of damage in the higher-dose MVIIA OCT treated animal was only 25% of that in untreated animals. The GVIA peptide also produced more than a 50% reduction in damage, and the lower dose was near maximal effectiveness.

Ischemia in the rat model system was induced by first surgically closing the vertebral arteries, and after surgical recovery, transiently blocking the carotid arteries (thus completely blocking blood flow to the brain) for a period of 15 minutes. During occlusion, animals were given 0.3 μg OCT MVIIA peptide ICV. Four days after occlusion, the animals were examined histologically, as above, to determine the extent of damage in the hippocampal CA1 region, as above. The mean scores are given in Table 10 in Example 11. As seen, the extent of damage in the treated animals was only about ⅓ that in untreated animals.

B. Functional Activity Protection: Hyperactivity

One common consequence of cerebral ischemia in animals is hyperactivity, which can be seen as pacing (exploratory) behavior within a few hours of occlusion, and can be observed up to several days later. Hyperactivity in ischemic gerbils was monitored as described in Example 12. Briefly, gerbils were tested individually for 60 min, with cumulative activity counts recorded every 15 min for statistical analysis. Baseline activity was measured before surgery to ensure comparability of the different treatment groups on this measure, and activity measurements were made at 1 and 3 days after occlusion.

Figure 9:
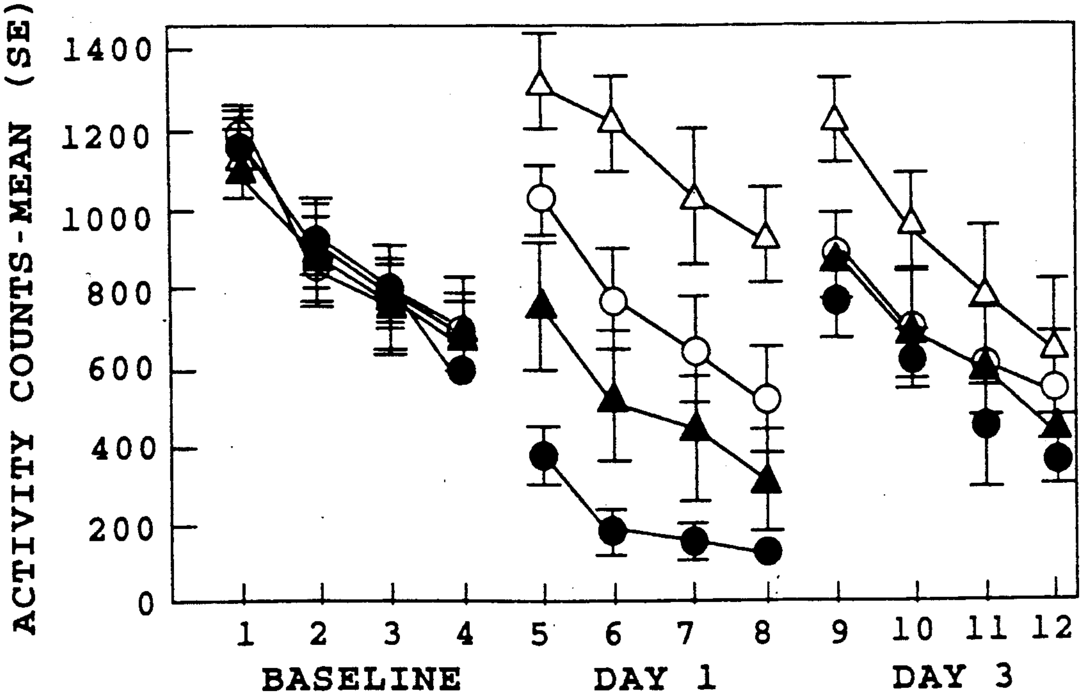
FIG. 9 plots the changes in spontaneous motor activity animals which were (a) unoccluded and untreated (open circles), (b) unoccluded and treated with MVIIA peptide(closed circles), (c) occluded but untreated (open triangles), and (d) occluded and treated with MVIIA peptide (closed triangles)

The results of the tests are plotted in FIG. 9. The downward slope in each test curve is due to the decrease in activity over the four 15 minutes intervals of the test (1-4 for baseline, 5-8 at day 1, and 9-12 at day three), as the animal becomes more familar with the test environment. Occlusion alone (open triangles) produced a significant rise in activity level over baseline levels 1 day after occlusion, and an elevated activity level was observed over a three-day period, indicating permanent behavioral damage. Non-occluded control animals receiving ICV administration of vehicle (open circles) remained at baseline activity levels through the test period. OCT peptide itself, in the absence of ischemia (solid circles) reduces activity, and this effect persists slightly even at three days. Occluded animals which had been treated with OCT MVIIA (solid triangles) showed lower-than baseline values at 1 day, apparently reflecting the reduced activity produced by the peptide alone. At three days, treated animals showed near-normal levels of activity, indicating that the OCT peptide treatment provided protection against ischemia-induced hyperactivity.

B. Functional Activity Protection: Spontaneous Alternation

One test which has been widely applied as a measure of short-term memory in experimental animals is the Y maze, in which animals are placed in the base of the stem of a Y "maze," and allowed to enter either of the two Y arms. When the animal enters an arm, a door is shut behind it. After 5 sec, the gerbil is returned to its home cage for an intertrial interval (ITI) of 2 to 12 min. At the end of that interval the animal is run in the maze again in the same way. Most normal animals will alternate, that is, will enter the arm that was not entered on the previous trial. The test is scored by a "Y" for alternation and an "N" for repeat selection of the same Y arm.

In the test procedure, ischemia in gerbils was induced as above, with simultaneous ICV administration of vehicle (control) or 0.1 or 0.3 μg OCT MVIIA or GVIA peptide (results from all drug treatments were combined, as described in Example 12). Three days after occlusion, the animals were tested in the Y maze. Results of the spontaneous alternation tests are summarized in Table 11 of the example for animals for which there was anatomical protection from doses of at least 0.1 μg of either compound.

As seen from the data in the table, the normal Y/N ratio for control animals (no occlusion, ICV administration of vehicle) was about 2:1. Ischemic injury produced a drop in this ratio to less than 1, indicating substantially random behavior in the Y test. The loss of short-term memory seen in ischemic animals was completely prevented by peptide treatment, with Y/N ratios of about 2:1 being obtained. Peptide alone in the absence of ischemic injury appeared to enhance the Y/N ratio, and this enhancement may contribute to the improved performance of treated, ischemic animals.

In summary, ischemic animals in which OCT peptide treatment was shown to significantly reduce anatomical damage, also showed statistically improved functional activity, as evidenced by peptide protection against ischemia-induced hyperactivity and loss of short-term memory.

IV. Binding/Inhibitory OCT Peptides

As noted above, the correlation between specific binding and inhibitory properties of OCT peptides and efficacy in treating ischemic allows for the selection and identification of OCT peptides based on the in vitro properties discussed in Section II. The binding/inhibitory OCT peptides, i.e., those which have the requisite in vitro binding and/or inhibitory properties, may be either natural OCT peptides or analogs thereof with amino acid substitutions which are compatible with the requisite binding and inhibitory activities of the peptide. This section describes constraints for amino acid substitutions in binding/inhibitory OCT peptide analogs.

A. Primary Structure Constraints

Based on a sequence homology analysis of seven of the peptides whose full sequences are known (FIG. 1), the active natural OCT peptides were grouped into two distinct groups, each with internal homologies distinct to that group, as can be appreciated from FIG. 1. The two groups are designated "M," including the MVIIA, MVIIB, and SVIB peptides, and "G," including the GVIA, GVIIA, RVIA, and SVIA peptides.

The two groups of OCT peptides are arranged in FIG. 1 with their six Cys residues aligned, which places these residues at positions 1, 8, 15, 16, 20, and 28. To make this alignment, a gap was introduced at the 18 position of the G-group peptides, and at the 23 and 27 positions of the M-group peptides. In the analysis below, these gaps retain the assigned number shown in FIG. 1, even though they represent amino acid deletions in the respective groups of active OCT peptides.

The sequence variation in the two peptide groups, based on primary structure considerations alone, was analysed by adopting the following constraints:

1. The peptides in both groups include the Cys residues at position 1, 8, 15, 16, 20, and 28. Other Cys residues may be substituted at the positions indicated below only if they are selectively protected during oxidation of the peptide to form the three disulfide linkages.

2. The peptides in both groups include three disulfide linkages connecting the Cys residues at positions 1 and 16, 8 and 20, and 15, and 30. As described above, the disulfide bridges are preferably formed by air oxidation of the full sequence peptide in the presence of DTT without Cys-residue protection, but may also be formed by selective deprotection of each pair of Cys residues.

The ability of the peptide to form the three desired disulfide linkages would therefore require that the peptide, prior to disulfide bridging, be able to adopt a conformation which allows the three selected linkages, with or without the Cys protecting-group strategy discussed above. This constraint excludes amino acid variations which prevent or otherwise hinder the formation of the three selected bridges.

Constraints 1 and 2 preserve the basic conformation of the OCT peptides imposed by the three disulfide bridges.

3. The SVIA peptide sequence is used as a negative predictor, based on its low binding and inhibitory properties, as discussed above. This was done by including amino acid variations which are consistent among the other group-G peptides, but inconsistent with the SVIA sequence, and conversely, by excluding variations found in the SVIA peptide which are not found in the other group-G peptides.

4. Within each of the two peptide groups, the residue positions which are invariant are most likely to be retained. Thus, for the G group peptides, the position 2 Lys, position 4 4Hyp, position 5 Gly, position 19 Ser, position 23 Tyr, and the position 26 Lys are retained, so that the G-group peptides have a total of 12 invariant residues (plus a deletion at position 18). Similarly, among the M-group peptides, the position 2 Lys, position 4 Lys, position 5 Gly, position 13 Tyr, position 14 Asp, position 18 Gly, position 19 Ser, position 22 Arg, position 25 Gly, and position 26 Lys are retained, for a total of 16 retained positions (plus deletions at positions 23 and 27). It is possible, of course, that invariant residues may be substituted by closely related amino acids, such as an Arg to Lys substitution, or a Tyr to Phe substitution.

5. At each position within the two groups which exhibit variance, i.e., represented by two or more different amino acid variations, the variants are analysed for membership in a common amino acid class. The classes which were selected are six standard classes based on common side chain properties and highest frequency of substitution in homologous proteins in nature, as determined, for example, by a standard Dayhoff frequency exchange matrix (Schwartz). The six classes are Class I: Cys; Class II: Ser, Thr, Pro, 4Hyp, Ala, and Gly, representing small aliphatic side chains and OH-group side chains; Class III: Asn, Asp, Glu, and Gln, representing neutral and negatively charged side chains capable of forming hydrogen bonds; Class IV: His, Arg, and Lys, representing basic polar side chains; Class V: Ile, Val, and Leu, representing branched aliphatic side chains, and Met; and Class VI: Phe, Tyr, and Trp, representing aromatic side chains. In addition, each group may include related amino acid analogs, such as ornithine, homoarginine, N-methyl lysine, dimethyl lysine, or trimethyl lysine in class IV, and halogenated tyrosine in Group VI. Further, the classes may include both L- and D-stereoisomers, although L-amino acids are preferred for substitutions.

6. If the variants in natural peptides can be placed in a single class, the most probable amino acid substitution that can occur at that position involves a member of the identified class. In the G-group peptides, these single-class variations are found at position 3 (class II), position 11 (class II), and position IV (class III). In the M-group peptides, the single-class variations are found at position 24 (class II).

7. If the variants in natural peptides do not fall within a single class, the variants are examined for other common properties which may be shared by other members of two or more of the above classes. In particular, if the natural variants are in two or more of the groups II, III IV, all of which are relatively polar amino acids, substitution is permitted among all members of the three classes. Similarly, if the natural variants are in groups V and VI, both of which are relatively nonpolar, substitution may occur within all members of theses two groups. In the G-group peptides, these groupings are present at position 9 (polar), position 17 (polar), position 23 (polar), and position 29 (polar). In the M-group peptides, these groupings are present at position 6 (polar), and position 21 (polar).

9. If variants are found in both polar and nonpolar groups, the position is considered open to substutition. In the G-group peptides, these open positions are 10, 12, 13, and 21. In the M-group peptides, the open-substitution positions are 3, 11, and 12. The substitutions preferably include L-amino acids.

10. Positions 25, 27, 29, or 30 of the G-group peptides may include a deletion. Positions 21, 23, or 24 of the M-group peptides may include a deletion.

11. The C-terminal amino acid residue of the peptide is preferably amidated.

B. Binding and Charge Constraints

The necessary binding regions or domains of OCT peptides have been examined by binding studies on the OCT peptide fragments shown in FIG. 2. The binding constants for the several peptides, shown in Table 3 in Example 4, were determined from competitive displacement of MVIIA peptide in electricorgan synaptosomes, as previously described.

The peptide fragments whose $pK_i$'s are greater than 6 are those labeled 170, 162, 173, and 174. All of these peptides have the first 9 N-terminal amino acids of M-group OCT peptides, indicating that this region, which contains three Lys groups, is critical for binding activities in fish electric organ synaptosomes. Similarly, peptide fragments that did not include the first 9 N-terminals generally showed low binding activities in fish synaptosomes. Additional binding studies carried out in support of the invention indicate that substitutions of acidic amino acids (Glu, Asp) at any of the first 10 N-terminal amino acid residues severely reduces binding activity. Therefore, another constraint which is imposed on the amino acid variations given above is that Asp and Glu substitutions are forbidden at the 1–10 N-terminal positions.

Figure 10A:
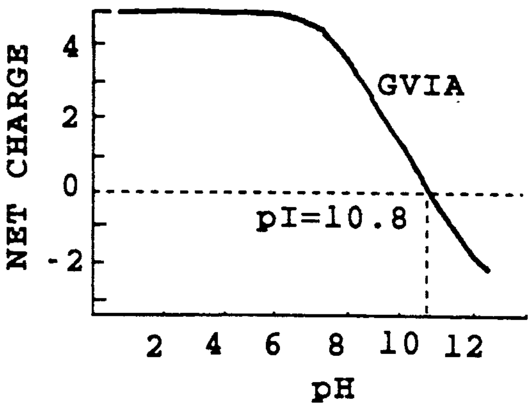
FIGS. 10A-10G are peptide charge/pH profiles for six OCT C-terminal amidated peptides.
Figure 10B:
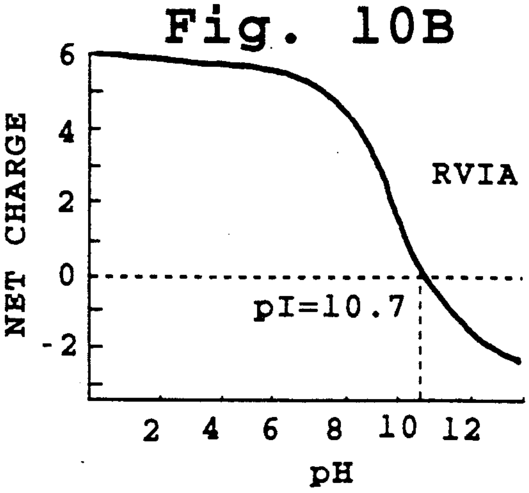
Figure 10C:
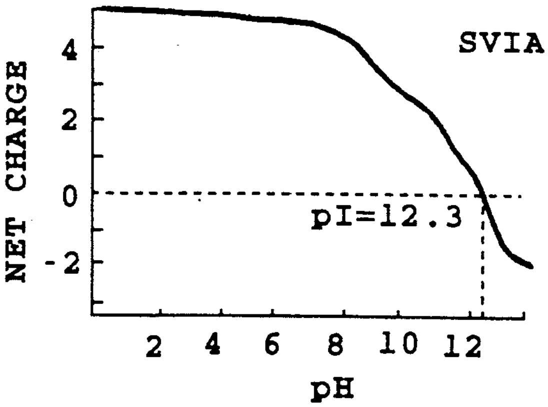
Figure 10D:
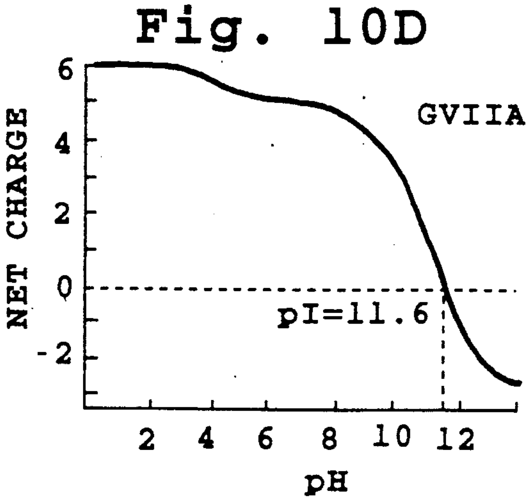
Figure 10E:
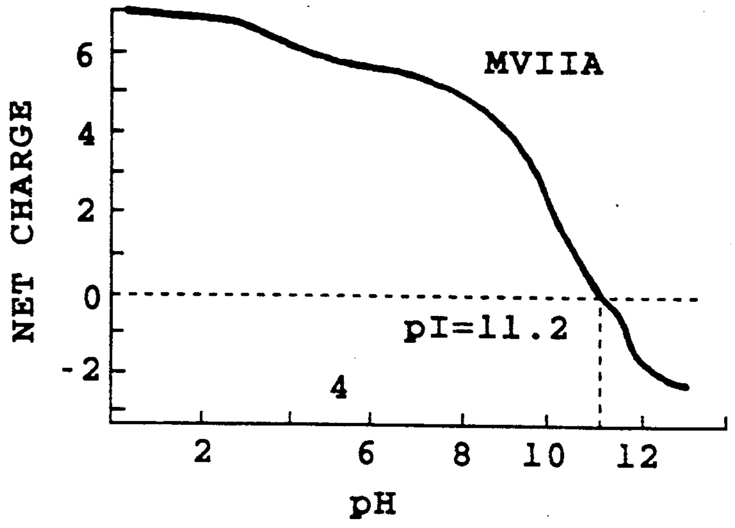
Figure 10F:
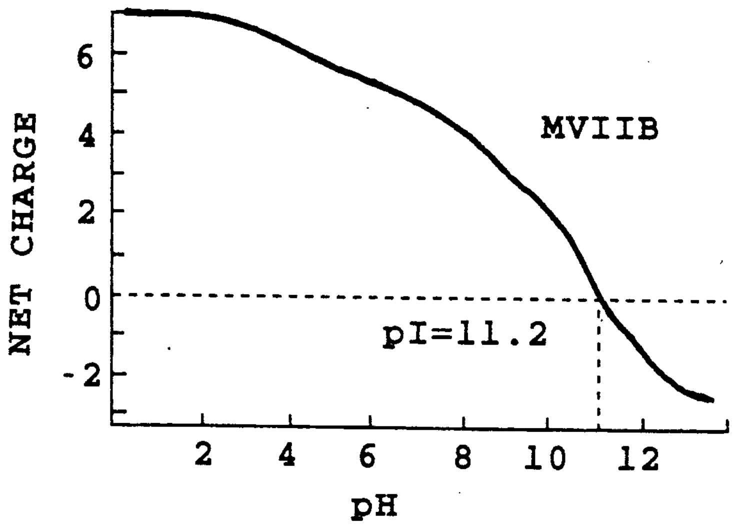
Figure 10G:
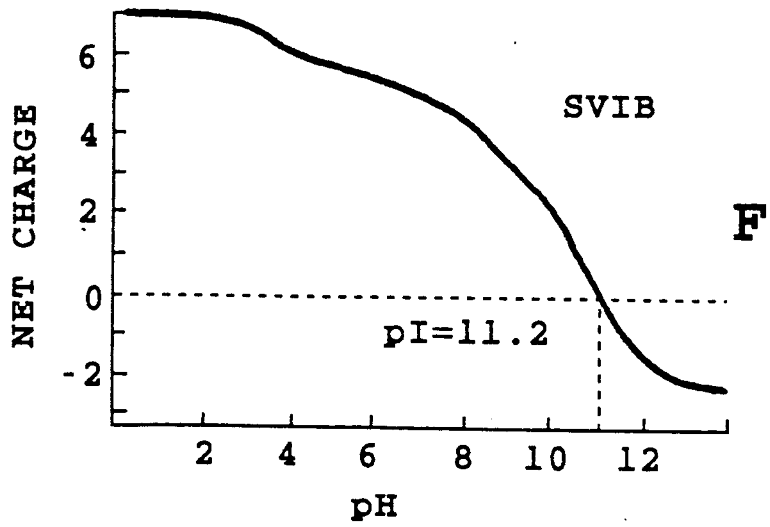
Figure 11A:
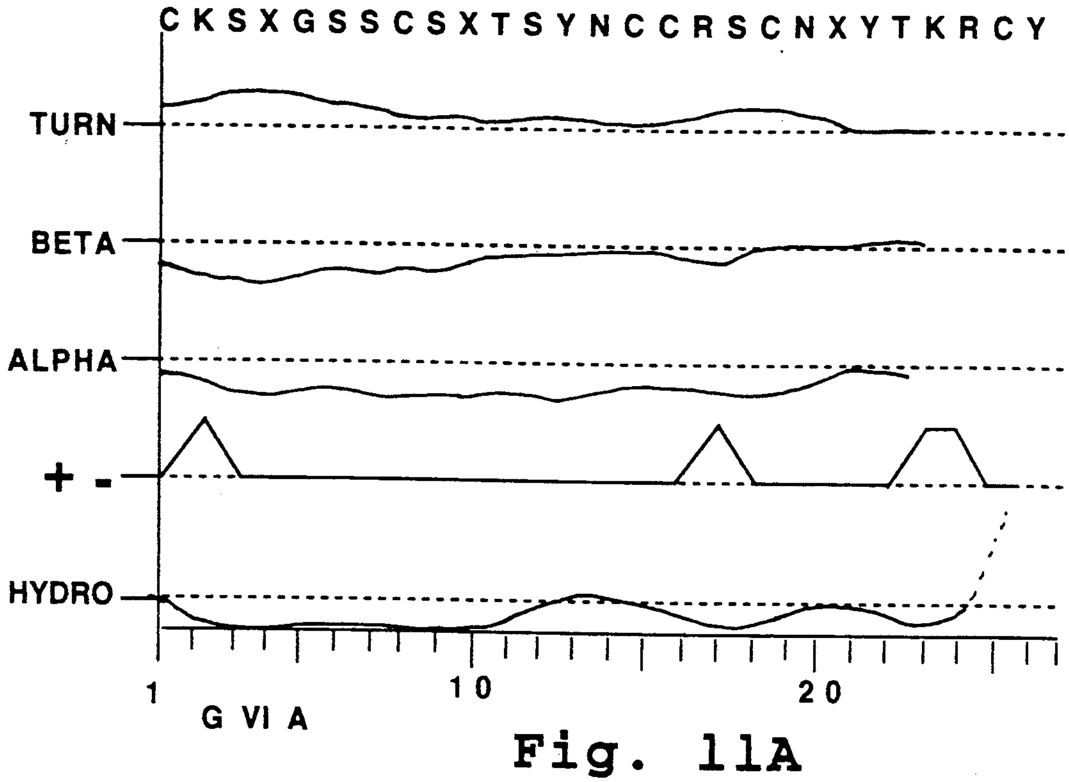
FIGS. 11A-11F are secondary structure plots for six OCT peptides.
Figure 11B:
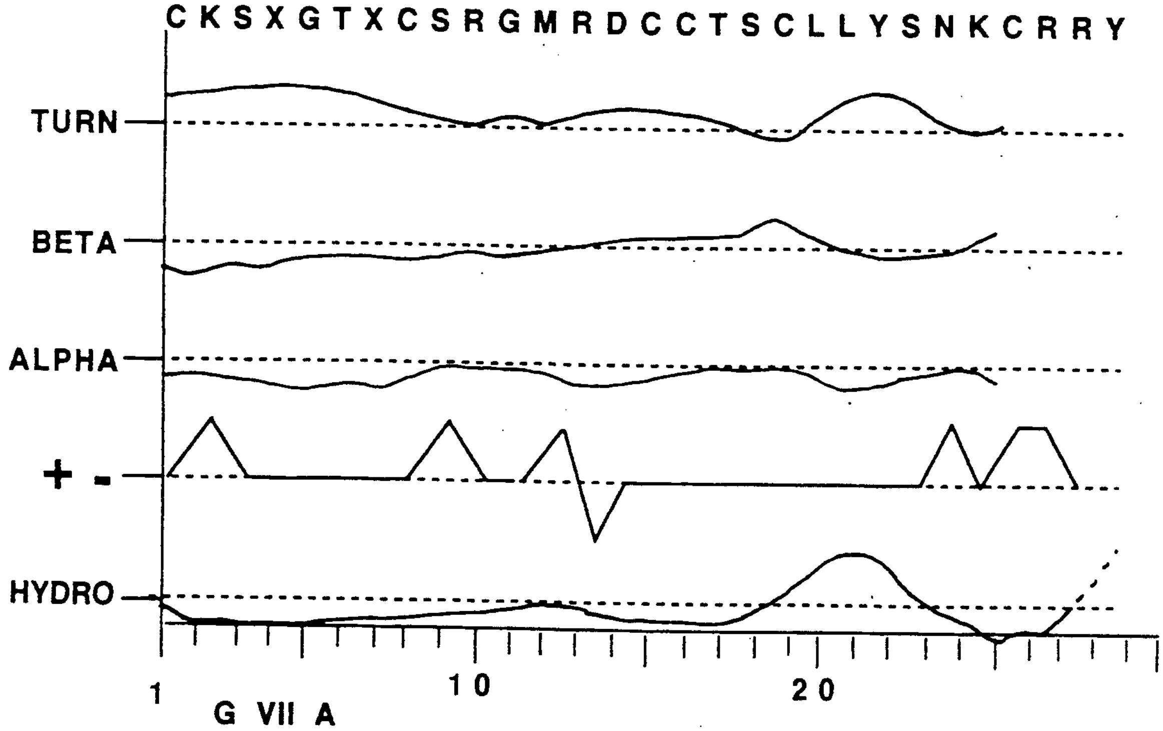
Figure 11C:
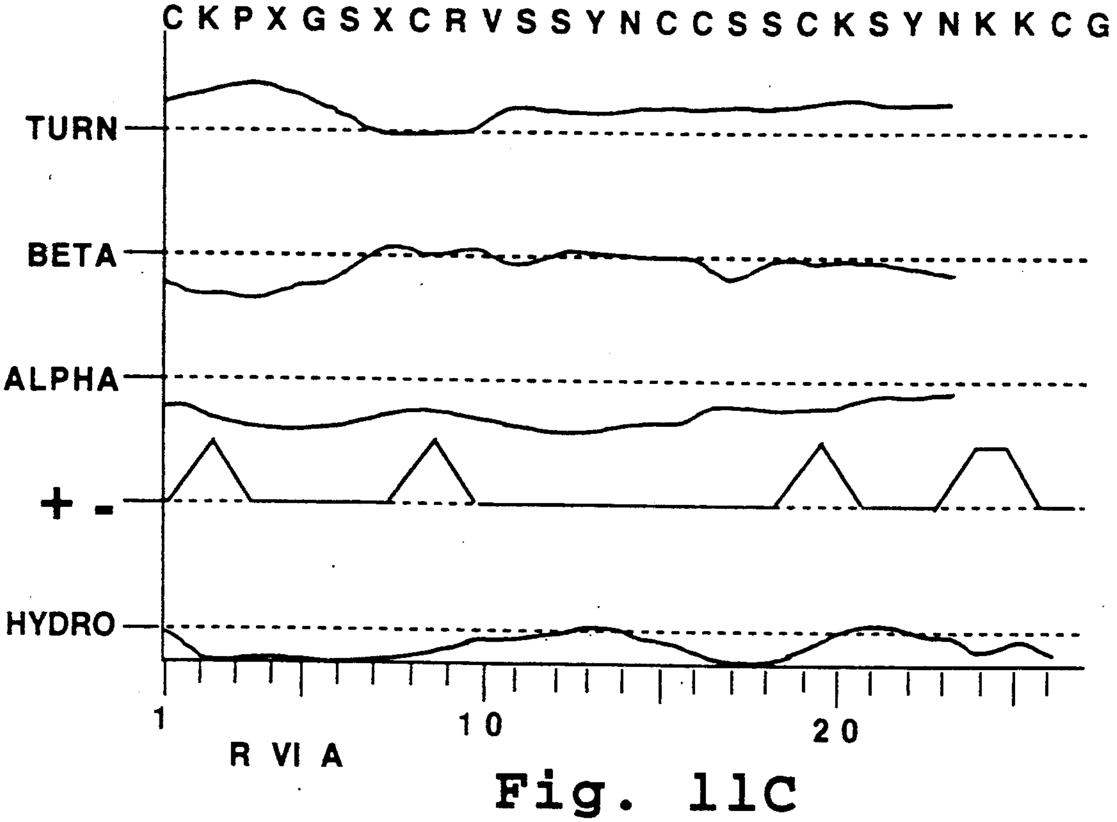
Figure 11D:
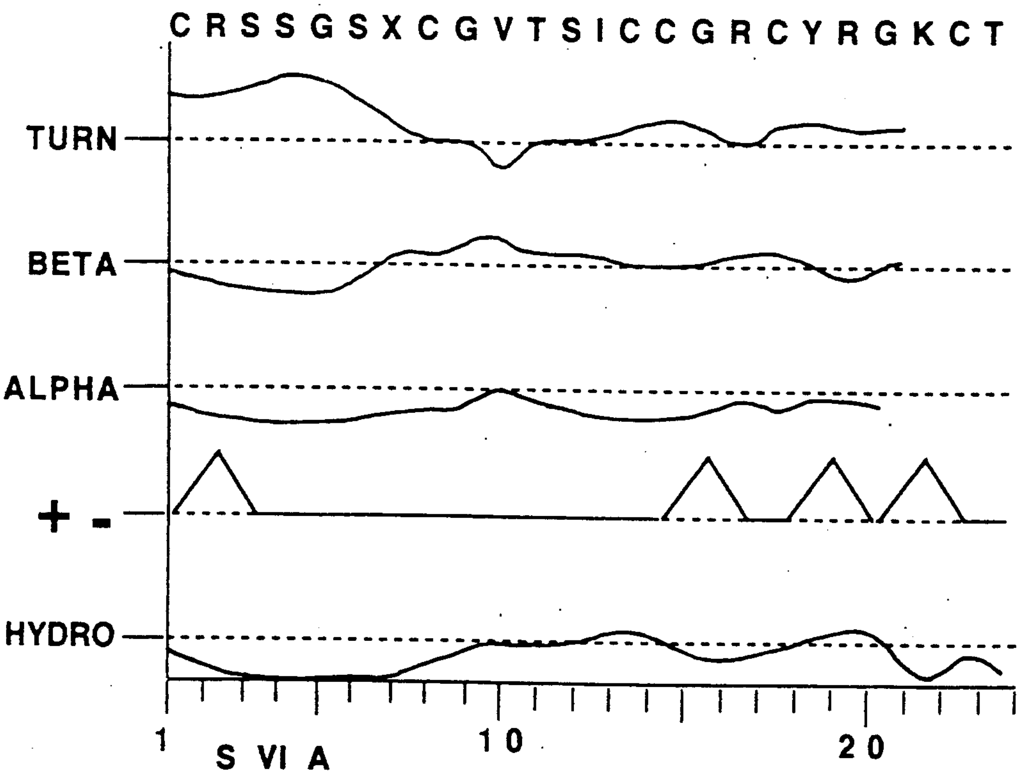
Figure 11E:
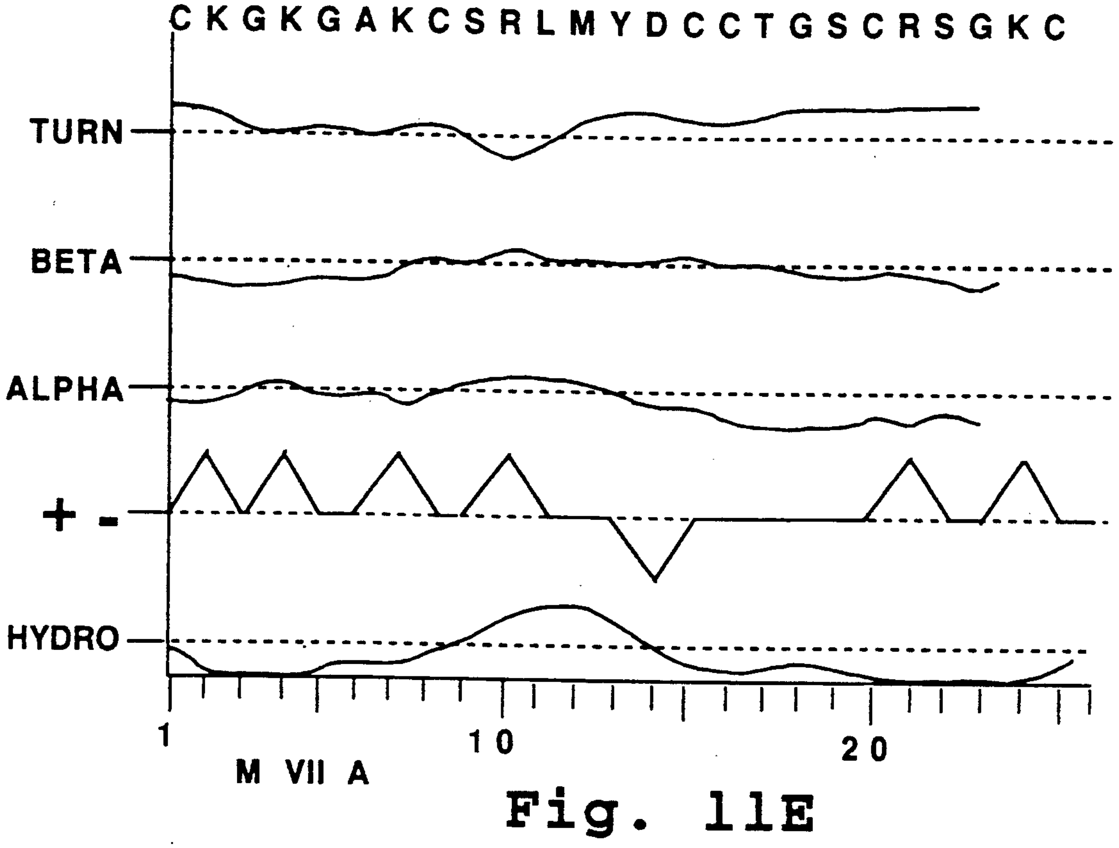
Figure 11F:
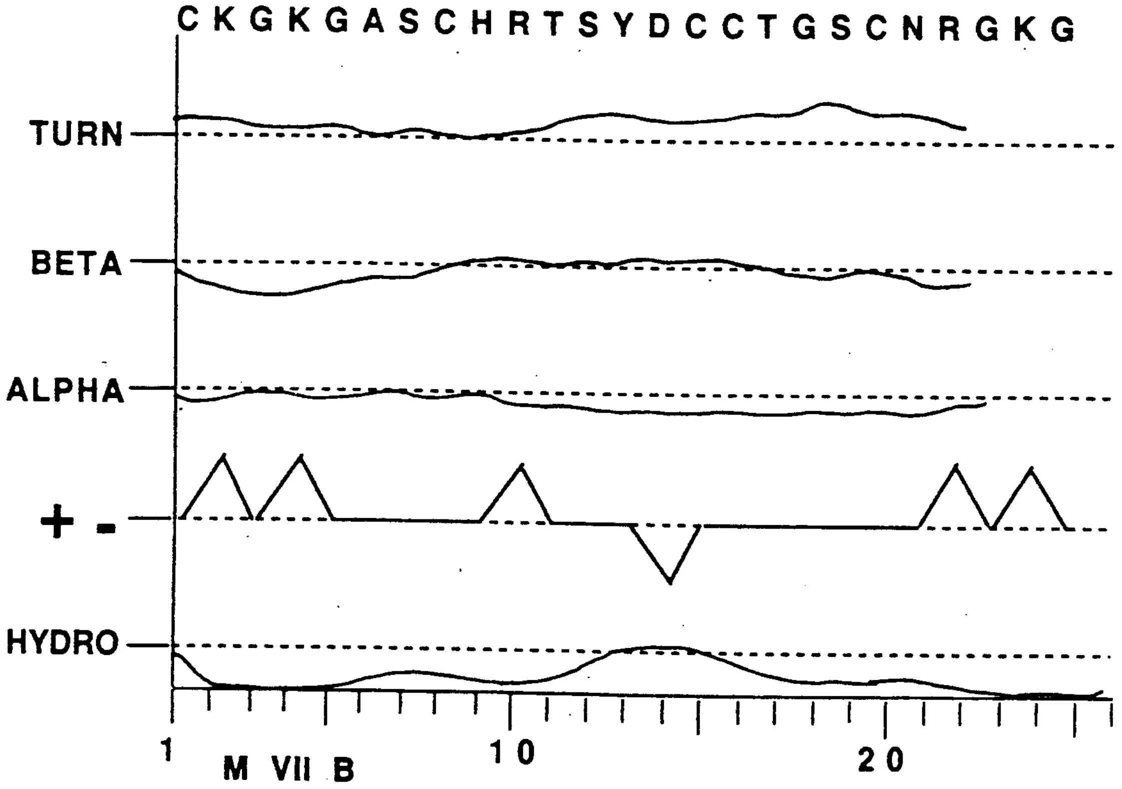

The net charge of OCT peptides has been plotted as a function of pH for several of the natural peptides, where the C-terminal amino acid is amidated. The plots, which are shown in FIGS. 10A–10B were constructed using standard pK's of the amino acids. As seen from the figures, all of the sequences examined which are active OCT peptides (all OCT peptides except SVIA) have isoelectric points between about 10.5 and 12. A further constraint, therefor, which may be imposed on the selection of amino acid variations in active peptides is the requirement for an isoelectric point between about 10.5 and 12. The M-group peptides (FIGS. 10E–10G) may be further constrained by the requirement for an isoelectric point between 11 and 12.

C. Secondary Structure Constraints

Several of the natural OCT peptide sequences were examined for secondary structure properties, using computer analysis programs available from Intelligenetics (Palo Alto, Calif.). The secondary structure prediction program known as NOVOTNY (Novotny) calculates the relative probability for a residue to adopt a helical or extended ($\beta$-sheet configuration), and the likelihood that the residue is part of a $\beta$-turn. The tendency to form helical or sheet states is determined using the method of Chou and Fasman (Chou), and this is then compared to the charge profile of the sequence (this is simply a map of the location of the charged residues and their associated charge). The probability values are averaged over groups of consecutive residues in a moving average to reduce random statistical fluctuations.

Secondary structure predictions can be made from these calculations. For example, regions having high $\beta$-turn potential, and charged residues, associated with low helix, sheet, and hydrophobicity probabilities are likely to be in a $\beta$-turn configuration. This is a non-quantitative method: it utility lies in comparing the relative tendencies of residues to hold different configurations, thus serving as a guide with which to judge possible secondary structures.

The analyses carried out with six of the OCT peptide sequences using the NOVOTNY program are shown in FIGS. 11A–11G. The alpha-helix and beta-sheet plots were considered only as features related to the folding of the peptide, prior to forming disulfide bridges, rather than as structures present in the mature peptide.

The plots in FIG. 11 were examined for particularly common secondary structure features. The most prominent of these are:

(a) a relatively low probability of alpha-helix and beta-sheet formation in the first 10 amino acid positions, and a correspondingly high likelihood of beta turn in the same region;

(b) a relatively low hydrophobicity over the first 8-10 amino acid positions, and an hydrophobicity peak in the region approximately between positions 12–15; and (c) for the G-group peptides, a second hydrophobicity peak in the region approximately between positions 19–25.

None of the above features are unique to the active peptides—i.e., present in the GVIA, GVIIA, RVIA, MVIIA, SVIB, and MVIIB, but not the SVIA, peptide—and therefore provide useful, but not sufficient constraints for evaluating possible amino acid substitutions which are consistent with binding/inhibitory activity in OCT peptide.

D. Tertiary Structure Constraints

The MVIIA peptide, which is exemplary of M-group OCT peptides, was studied by nuclear magnetic resonance (NMR) spectroscopy, to define distance relationships between selected proton sites in the peptide. The NMR method known as Two-Dimensional Nuclear Overhauser Effect (2D-NOE, or NOESY), was used. The NOE NMR phenomenon is based on the perturbation of the intrinsic magnetic fields of hydrogen nuclei by the presence of nearby hydrogen nuclei. The perturbation effect is transmitted through the space between the nuclei, and is inversely proportional to the sixth power of the distance between nuclei (Kessler). By measuring the NOE of the hydrogen nuclei in the sample, and correlating this measurement with the amino acids to which the hydrogen nuclei are attached, distance relationships between pairs of hydrogen nuclei, typically associated with the amide nitrogen proton, can be determined. The maximum proton/proton spacing which can be detected is about 5 angstroms.

The following pairs of amino acids given below represent proximate amino acid pairs in which the amide hydrogens (or otherwise as indicated) in the paired residues give detectable long-range (about 4.5 angstrom) or shortrange (about 2.5 angstrom) distance couplings:

Long-range:
Lys (position 2) and Cys (position 16)
Gly (position 5) and Cys (position 28)
Lys (position 26) and Cys (position 20)
alpha H Cys (position 28) and Gly (position 18)
beta H Cys (position 28) and Lys (position 2)
alpha H Lys (position 26) and Cys (position 8)
beta H Cys (position 1) and Cys (position 16)
beta H Cys (position 28) and Gly (position 5)
beta H Cys (position 28) and Gly (position 18)

Short-range:
Ser (position 24) and Gly (position 25)
Asp (position 14) and Cys (position 15)
Tyr (position 13) and Asp (position 14)
Gly (position 25) and Lys (position 26)

These distance constraints can be used to generate a minimum-energy 3-D configuration of the protein using one of a variety of commercially available molecular dynamics (MD) programs, such as the computer modelling program available from by Biosym TM (San Diego, Calif.). 3-D models of the MVIIA have been generated using the Biosym TM program. Amino acid substitutions can be tested in this modelling system by allowing the system to reach a new energy minimum, with the substituted amino acid residue(s), and determining whether the above distance constraints are preserved.

The above subsections A–D provide criteria for selecting amino acid substitutions in natural binding/inhibitory OCT peptides. Assuming a proposed amino acid substitution meets the criteria set forth in these subsections, the peptide can be synthesized and tested for in vitro binding or inhibitory activity, as described in Section II, to confirm that the peptide has the desired binding/inhibitory properties.

The following examples are intended to illustrate methods for preparing OCT peptides, test methods for determining in vitro and in vivo binding and inhibitory activities, and exemplary treatment results. The examples are in no way intended to limit the scope of the invention.

EXAMPLE 1

Preparation of MVIIA OCT Peptide

Abbreviations used in this example are BOC, tertiary butoxycarbonyl; DCM, dichloromethane; TFA, trifluoroacetic acid; IPM, N-isopropylmorpholine; BOC-AA-OH, BOC amino acid; DIEA, diisopropylethylamine; 2-ClZ, 2-Chlorobenzyloxycarbonyl; tosyl, p-toluenesulfonyl; DMF, N,N-dimethylformamide; TFE, trifluoroethanol; SA, symmetrical anhydride of BOC-AA-OH; DCCI, N,N-dicyclohexylcarbodiimide; DCM, dichloromethane; E, ethyl ether; P, petroleum ether; 2-BrZ, 2-bromobenyloxycarbonyl.

Commercially available benzhydrylamine-resin hydrochloride, Lot No. B30101, was obtained from Beckman Instruments Inc., Palo Alto, Calif. With this resin, cleavage of a peptide formed on the resin, under the conditions described below, produces a peptide which is amidated at its carboxy end.

A. Preparing Protected Amino Acid Anhydrides

Each BOC-AA-OH (2.4 mmol) was dissolved in 5 ml DCM and cooled to 0° C. The volume of DCM used for BOC-Leu-OH (dried in vacuo) was 12 ml, and the BOC-Leu-OH solution was not cooled. 2 ml 0.6M DCCI in DCM was added and the mixture stirred at 0° C. for 15 min. For BOC-Leu-OH, the mixture was also cooled after this addition. Precipitation of N,N,-dicyclohexylurea was completed by storage at −20° C. for 1.5 hour, after which the precipitate was filtered and washed with ethyl ether (5 ml). The filtrate was evaporated to remove solvents and the product was crystallized in the solvent system given in Table 1. Residual amounts of DCM can affect the exact conditions for crystallization. Recrystallization was performed by dissolving in DCM, evaporating most of the solvent, and recrystallizing from the appropriate solvent.

TABLE 1

| Amino Acid | Solvent |
|---|---|
| Ala | DCM |
| Asp (Benzyl) | E:P |
| Cys (4-MeBenzyl) | DCM |
| Gly | E:P |
| Leu | P |
| Lys (2-ClZ) | E:P |
| Met | E:P |
| Ser (Benzyl) | E:P |
| Thr (Benzyl) | E:P |
| Tyr (2-BrZ) | DCM |

B. Coupling Procedure

Synthesis of MVIIA peptide was performed in a Beckman Model 990 Peptide Synthesizer by a solid-phase method based on the following primary structure: HCysLysGlyLysGlyAlaLysCysSerArgLeuMetTyrAspCysCysThrGlySer CysArgSerGlyLysCys$NH_2$.

A double coupling protocol was used for the incorporation of residues Cys-28 through Tyr-13, and a triple coupling protocol, for amino acids Met-12 through Cys-1. Symmetrical anhydrides were used in crystalline form according to published methods described in (Yamashiro). Crystalline symmetrical anhydrides (1.0 mmole) were each dissolved in 6 ml DCM and stored in the amino acid reservoirs at 4° C. Side-chain protecting groups used were: Cys, 4-MeBenzyl; Lys, 2-ClZ; Ser, Benzyl; Arg, Tosyl; Thr, Benzyl; Asp, Benzyl; Tyr, 2-BrZ.

Unless specified, volumes were 8 ml, except for step 2 below, which was 10 ml, and all reactions were carried out at room temperature. After incorporation of the Asp-14 residue, the volume of step 2 was increased to 15 ml while all other volumes were raised to 10 ml after incorporation of the Arg-10 residue. The double coupling protocol consisted of steps 1-16 listed in Table 2 below.

Amino acids Met-12 through Cys-1 were added by a triple coupling protocol which included, in addition to steps 1-16, steps 17-19 in Table 2.

TABLE 2

| Step | Reagent |
|---|---|
| 1 | DCM wash (3 times) |
| 2 | 67% TFA/DCM (20 min.) |
| 3 | DCM wash (2 times) |
| 4 | 25% dioxane/DCM wash (2 times) |
| 5 | 5% DIEA/DCM wash |
| 6 | DCM wash |
| 7 | 5% DIEA/DCM wash |
| 8 | DCM wash (5 times) |
| 9 | 1.0 mmol SA in DCM (5 min) |
| 10 | 0.5 mmol IPM in 3 ml TFE plus 1 ml DCM (5 min) |
| 11 | 0.5 mmol IPM in 5 ml DCM (5 min) |
| 12 | DMF wash (3 times) |
| 13 | 1.0 mmol SA in DMF (5 min) |
| 14 | 0.5 mmol IPM in 5 ml DCM (5 min) |
| 15 | 0.5 mmol IPM in 4 ml DMF (5 min) |
| 16 | DCM wash |
| 17 | DCM wash (2 times) |
| 18 | 1.0 mmol SA in DCM (5 min) |
| 19 | 0.5 mmol IPM in 4 ml DMF (5 min) |

Crystalline symmetrical anhydrides (1 mmole) were each dissolved in 6 ml DCM or DMF and stored in the amino acid reservoirs at 4° C. Side-chain protecting groups used were: Cys, 4-MeBzl; Lys, 2-ClZ; Ser, Bzl; Arg, tosyl; Thr, Bzl; Asp, Bzl; Tyr, 2-BrZ.

For BOC-Arg(tosyl)-OH, the following mixture was prepared: 1.87 BOC-Arg(tosyl)-OH, 0.57 g 1-hydroxybenzotriazole, 15 ml DMF, stirred to dissolve, cooled to 4° C., added 0.52 ml diisopropylcarbodiimide, and split in half for steps 9 and 13. For this coupling, the protocol was modified as follows: step 8 was 3 times DCM wash and 2 times DMF wash; step 9 was for 10 min; step 11 was for 10 min; step 13 was for 10 min; step 14 was 0.4 mmol IPM in 4 ml DMF for 10 min; step 15 was for 10 min; step 16 was 1 times DMF wash and 1 time DCM wash. Reaction mixtures in steps 9, 10, 13, 14 and 18 were not drained.

The mixture for a third coupling for incorporating the Arg-10 residue consisted of 1.00 g BOC-Arg(tosyl)-OH, 1 ml DMF, 5 ml DCM, stirred to dissolve, and cooled to 4° C. to which is then added 1.67 ml 0.6M DCCI in DCM.

After the last amino acid had been incorporated, the protected peptide resin was subjected to steps 1-4 to remove the N-terminal BOC group, collected on a filter with use of ethanol, and dried in vacuum to yield 2.61 g.

C. Deblocking and cleavage in liquid HF

A mixture of protected peptide resin (1.32 g), 2-mercaptopyridine (0.50 g), p-cresol (2.6 g), and liquid hydrogen fluoride (HF) (25 ml) was stirred at 0° C. for 80 min. The liquid HF was evaporated with a rapid stream of nitrogen gas, first below 0° C., then at 24° C. The mixture was stirred in ethyl acetate (25 ml) until a finely divided solid was obtained. The solid was filtered, washed with ethyl acetate, and air dried to yield 1.09 g. This solid was stirred in 50% aqueous acetic acid (10 ml) to dissolve the peptide material, filtered, and washed with 20 ml water. The filtrate was freeze-dried to yield 450 mg of fluffy powder.

D. Formation of disulfide bridges

A sample (300 mg) of the fluffy powder was dissolved in 30 ml of 0.05M ammonium bicarbonate, 10 mM dithiothreitol (DTT), and 2M guanidine hydrochloride. The solution, which had a pH of 6.7, was allowed to stand at 24° C. for 2 hr, then diluted with 120 ml of water and stirred for 20 hr at 24° C. DTT (25 mg) was added and the solution allowed to stand at 24° C. for 80 min. The mixture was then stirred at 4° C. for 3 days.

E. Isolation of MVIIA OCT

The solution from Part D was acidified with glacial acetic acid (2 ml), evaporated in vacuo to a low volume, and fractionated by gel filtration on Sephadex G-25 in a 2.5×48 cm column, using 1N acetic acid, to remove peptide polymeric species (exclusion volume), and salts (slowest moving peak). Fractions (5 ml) were collected, with peptide absorbance monitored at 280 nm. Fractions corresponding to the monomer peptide were pooled and freeze-dried to give 127 mg of fluffy powder. A sample of the monomeric material (34 mg) was purified by preparative HPLC on a Vydac 218TP1022 column with a gradient of 10-20% acetonitrile in 0.1% trifluoroacetic acid over 50 min at 8 ml/min, with detection at 226 nm and collection of 4 ml fractions. Fractions corresponding to the major peak were pooled, evaporated in vacuo to remove acetonitrile, and freeze-dried to yield 7.7 mg. Analytical HPLC on a Vydac 218TP104 column with the same solvent and gradient over 10 min followed by 10 min of isocratic elution at the 20% composition (1.5 ml/min) gave a single peak identical in behavior to an authentic sample of OCT MVIIA. Amino acid analysis of a 24-hr HCl-hydrolysate gave: Asp, 0.93; Thr, 1.05; Ser, 2.85; half-cystine, 5.2; Gly, 4.08; Ala, 1.07; Met 0.94; Leu, 1.02; Tyr,0.85; Lys, 3.98; Arg, 2.09.

F. Radio-Iodination of MVIIA

MVIIA peptide was iodinated by reaction with Iodogen TM in the presence of NaI according to Cruz et al., with minor modification. 2 m Ci of carrier-free $Na^{125}I$, 75 ul 0.5M phosphate buffer pH 7.4 and 20 ul of 1 ug/ul peptide were added to a polypropylene test tube coated with 10 ug Iodogen TM. The tube was agitated for 8 minutes, and the solution was chromatographed by HPLC through a 10×0.46 cm C-8 reverse phase column with a pore size of 300 Å (Brownlee Labs, Santa Clara, Calif.). The sample material was eluted with a gradient from 0.1% trifluoroacetic acid to 60% acetonitrile in 0.1% trifluoroacetic acid. The major peak of active radio-iodinated peptide was resolved at about 2 minutes greater retention time than the underivatized peptide.

The fractions containing this peak were collected and later diluted for use in binding experiments. MVIIA, iodinated under the conditions as above except with non-radioactive NaI, was tested for the ability to inhibit depolarization-dependent ATP release from synaptosomes, using the method described in (Ahmad). The iodinated MVIIA peptide was found to be as potent in this regard as the underivatized peptide.

EXAMPLE 2

Preparation of GVIA, SVIA, GVIIA, SVIB, and RVIA OCT Peptides

Syntheses of GVIA, SVIA, MVIIB, GVIIA, and RVIA OCTs were based on the following sequences, which are shown in FIG. 1:

GVIA: HCysLysSer4HypGlySerSerCysSer4HypThrSerTyrAsnCysCysArgSerCysAsn4HypTyrLysArgCysTyr-$NH_2$.

SVIA: H-CysArgSerSerGlySer4HypHisCysGlyValThrSerIleCysCysGly ArgCysTyrArgGlyLysCysThr-$NH_2$.

MVIIB: H-CysLysGlyLysGlyAlaSerCysHisArgThrSerTyrAspCysCysThr GlySerCysAsnArgGlyLysCys-$NH_2$.

GVIIA: H-CysLysSer4HypGlyThr4HypCysSerArgGlyMetArgAsp CysCysThrSerCysLeuLeuTyrSerAsnLysCysArgArgTyr-$NH_2$.

RVIA: H-CysLysPro4HypGlySer4HypCysArgValSerSerTyrAsnCys CysSerSerCysLysSerTyrAsnLysLysCysGly-$NH_2$.

SVIB: H-CysLysLeuLysGlyGlnSerCysArgLysThrSerTyrAspCysCysSerGlySerCys-GlyArgSerGlyLysCys-$NH_2$.

Synthesis of each OCT was performed according to the solid-phase method described in Example 1, except that a single coupling protocol involving steps 1–12 in Example 1, Part C was used for coupling the first 10 C-terminal amino acids residues, and a double coupling method involving steps 1–16 in Example 1, Part C was used for coupling the remaining N-terminal residues-.oosefi Releasing the peptide from the solid support, removing the blocking groups, and joining the disulfide bridges were carried out substantially as above. The peptide was separated from salts and polymeric peptide species by gel filtration on Sephadex G-25, and purified on preparative HPLC as described in Example 1. For binding studies, each peptide can be radioiodinated essentially as above.

EXAMPLE 3

Preparation of OCT Peptide Fragments

The following peptide sequences, representing the aligned portions of the MVIIA OCT peptide, as shown in FIG. 2, were synthesized, where boldface A is Ala replacing Cys, and X is 4Hyp:

| | |
|---|---|
| MVIIA: | C K G K G A K C S R L M Y D C C T G S C R S G K C—$NH_2$ |
| 160: | ............................ C C*T G S C*R S G K C—$NH_2$ |
| 161: | ............... C S R L M Y D C*C*T G S C—$NH_2$ |
| 162: | C K G K G A K C*...................... C*R S G K C—$NH_2$ |
| 163: | C K G K G A K C*S R L M Y D C*C—$NH_2$.................. |
| 170: | C K G K G A K C S R—$NH_2$............................... |
| 171: | C K G K G A K **A** S R L M Y D **A** C—$NH_2$................. |
| 172: | C K G K G A K C S R L M Y D C C—$NH_2$................. |
| 173: | C K G K G A K C*S R L M Y C*C—$NH_2$................. |
| 174: | K G K G A K S R—$NH_2$............................. |
| 175: | C K G K G A K ...................... R S G K C—$NH_2$ |
| 176: | C K S K G S K ...................... R S G K C—$NH_2$ |
| 179: | C K G K G A K S X L M Y D **A** C—$NH_2$ |

*means protected cysteine residue (Cys-acetomidomethyl).

The following peptide sequences, representing the aligned portions of the GVIA OCT peptide, were synthesized:

| | |
|---|---|
| GVIA: | C K S X G S S C S X T S Y N C C R S C N X Y T K R C Y—$NH_2$ |
| 177: | C K S X G S S **A** S X T S Y N **A** C—$NH_2$.................... |
| 180: | C K S X G S S **A**.................... **A** N X Y T K R C Y—$NH_2$ |

Synthesis of each OCT peptide fragment was performed according to the solid-phase method described in Example 1, except that a single coupling protocol involving steps 1–12 in Example 1, Part C was used for coupling all of the residues in the each fragment.

Releasing the peptide fragment from the solid support, removing the blocking groups, and joining the disulfide bridges were carried out substantially as above. The peptide fragments were purified on preparative HPLC as described in Example 1, Part E.

EXAMPLE 4

Competitive Peptide Binding to Fish Synaptosomes

A. Preparation of Fish Synaptosomes

Electric organ synaptosomes were prepared by dissection from marine electric rays (*Ommata dyscopyge*) that had been stunned with 0.25 g/liter tricaine HCl and cooled to 4° C. immediately prior to dissection. All subsequent manipulations were carried out at 0°–4° C. whenever possible. Organs were diced and homogenized for 4 15-second periods in a Waring blender with an equal weight of plain synaptosome buffer (PSB) consisting of 280 mM NaCl, 3 mM KCl, 1.8 mM $MgCl_2$, 300 mM urea, 100 mM sucrose, and 5.5 mM glucose in 20 mM HEPES containing 5 mM Mg-EGTA at pH 7.2.

The homogenate was loaded into a 60 ml syringe, force filtered through a 40-mesh stainless-steel screen and centrifuged at 30,000×g for 15 min. The supernatant was discarded and the pellet taken up in 20 ml PSB. The resuspended pellet was further disrupted with 5 strokes of a loose-fitting Teflon pestle in a glass homogenizer and then centrifuged at 400 rpm. The resulting suspension was centrifuged once more at 30,000×g for 15 min. The supernatant was discarded at the pellet resuspended with the Teflon-glass homogenizer by 10 passes of the pestle at 400 rpm. This homogenate was layered onto six 32 ml 3–20% Ficoll gradiants in PSB and centrifuged at 76,6000×g for 1 hour in a swinging bucket rotor. The synaptosome band (the first band below the buffer-gradient interface) of each gradient was aspirated off and diluted at more than 1:1 with PSBG25. The diluted synaptosome suspension was pelleted at 30,000×g for 15 min and resuspended in 1 ml PSB.

B. Competitive Binding Assay

The OCT peptides and peptide fragments whose synthesis is described in Examples 1-3 were tested for binding to elasmobranch electric organ synaptosomes (also referred to herein as fish synaptosomes), using a competitive binding assay based on displacement of radiolabeled OCT MVIIA by the test peptide or peptide fragment. Total binding was measured using $^{125}$I-MVIIA OCT alone, and non-specific binding was determined by measuring $^{125}$I-MVIIA OCT bound in the presence of 1 uM unlabeled MVIIA. The difference between these values constituted $^{125}$I-MVIIA OCT specifically bound to OCT binding sites.

The binding constant ($K_d$) for MVIIA OCT to fish synaptosomes was determined by a saturation binding method in which increasing quantities of the OCT were added to aliquots of a synaptosome preparation. The amount of labeled peptide specifically bound at each concentration was used to determine $B_{max}$, the concentration of specific binding sites on the synaptosomes, and $K_d$, following standard binding analysis methods (Bennett).

In the competitive binding assays, binding was initiated by adding a quantity of synaptosomal membranes (5-10 μg protein) suspended in 400 ul binding medium to a series of tubes containing both 50-275 pM 125I-MVIIA and test substances ranging in concentration from approximately $10^{-3}$M to $10^{-13}$M. An additional tube containing 1 uM unlabeled MVIIA OCT was included to measure non-specific MVIIA binding. Binding medium consisted of 0.1 mM EDTA, 0.1 mM EGTA, 1 mM PMSF, 2 uM leupeptin, 1 uM pepstatin, and 125 mM NaCl in 20 mM HEPES (pH 7.4) containing 0.1% gelatin. Final assay volume was 500 ul. Assay tubes were incubated for 100 minutes at 4° C. on a rotating mixer.

Separation of bound $^{125}$I-MVIIA OCT from unbound peptide was achieved by rapid vacuum filtration of 150 ul aliquots of binding mixture from each tube through Whatman GF/C glass-fiber filters presoaked in an aqueous solution containing 0.6% polyethylenimine. Tissue-bound $^{125}$I-MVIIA OCT retained on the filters was washed three times with 3.5 ml of ice-cold wash buffer consisting of 20 mM HEPES (pH 7.4), 125 mM NaCl, and 0.1% gelatin. Filters were dried and their radioactivity measured in an LKB gamma counter at 75% counting efficiency.

The binding constant $K_i$ for each test substance was calculated using non-linear, least-squares regression analysis of competitive binding data from 2 assays performed in duplicate on separate occasions, and employing the $K_d$ value determined for the MVIIA OCT, according to reported $K_i$ analysis procedures (Bennett). Approximate $K_i$ values and corresponding pKi values for the test peptides are shown in the table.

TABLE 3

| Compound | Ki | pKi |
|---|---|---|
| MVIIA | 0.40 nM | 9.4 |
| MVIIB | 22 nM | 7.66 |
| GVIA | 14 nM | 7.85 |
| SVIA | >>1 mM | <3 |
| RVIA | 324 nM | 6.45 |
| GVIIA | 3.1 nM | 8.51 |
| SVIB | 3.0 nM | 8.52 |
| MVIIA 170 | 280 nM | 6.55 |
| MVIIA 171 | 4.6 μM | 5.33 |
| MVIIA 161 | >>1 mM | <3 |
| MVIIA 160 | 120 μM | 3.92 |

TABLE 3-continued

| Compound | Ki | pKi |
|---|---|---|
| MVIIA 162 | 170 nM | 6.77 |
| MVIIA 174 | 530 nM | 6.28 |
| MVIIA 172 | 20.9 μM | 4.68 |
| MVIIA 173 | 720 nM | 6.14 |
| MVIIA 179 | >>1 mM | <3 |
| MVIIA 163 | 217 μM | 3.66 |
| MVIIA 175 | 3.6 μM | 5.44 |
| MVIIA 176 | 1.8 μM | 5.74 |
| GVIA 177 | >>1 mM | <3 |
| GVIA 180 | 123 μM | 3.91 |

EXAMPLE 5

Competitive Peptide Binding to Mammalian-Brain Synaptosomes

A. Preparing Rat Brain Membranes

Rodents were sacrificed by cervical dislocation and their brains quickly removed, weighed, then transferred to approximately 10 ml ice-cold 0.32M sucrose, and homogenized two brains at a time with a motor-driven Teflon glass homogenizer. Homogenates were transferred to two 40 ml centrifuge tubes and spun at 950×g for 10 minutes at 4° C. Supernatants were transferred to two 40 ml tubes and recentrifuged at 8,500×g for 15 minutes. The resulting supernatants were discarded and the pellets were resuspended in 10 ml ice cold 0.32M sucrose by vortexing. Suspensions were combined and recentrifuged at 8,500×g for 15 minutes. After removing and discarding the supernatant, the pellet was resuspended in 20 ml ice-cold 0.32 M sucrose plus protease inhibitors, and the mixture was layered in 5 ml aliquots over four stepped sucrose density gradients in 35 ml ultracentrifuge tubes. Centrifugation was at 150,000×g for 60 minutes at 4° C. in a swinging bucket rotor.

After centrifugation, top layers were aspirated off; the 1.0M sucrose layer and the material at the 1.0M-1.2M sucrose interface were collected, and centrifuged at 30,000×g for 15 minutes. Pellets were resuspended in 3 volumes of ice cold water, (Polytron setting 6, 10 seconds) then recentrifuged at 40,000×g for 15 minutes. Supernatants were discarded and pellets were resuspended in 5 ml ice-cold distilled water. Aliquots of this suspension were frozen at −120° C. until used.

The competitive binding assay was performed substantially as described in Example 4B, for MVIIA OCT. Computer-fit competitive binding curves for 2 assays performed in duplicate on separate occasions are shown in FIG. 3. Assuming a single binding site, a four-parameter logistic function fitted to the data yielded the $IC_{50}$ values (OCT peptide concentration at which half the labeled NVIIA OCT is displaced by the test peptide) shown below in Table 4.

TABLE 4

| OCT peptide | $IC_{50}$ [nM] |
|---|---|
| MVIIA | 0.019 |
| MVIIB | 0.49 |
| GVIA | 0.48 |
| SVIB | 5.7 |
| GVIIA | 22.9 |
| RVIA | 229. |
| SVIA | >>1 mM |

EXAMPLE 6

Binding of MVIIA to Cultured Neuronal Cells

A. Preparing Cultured Neuronal Cells

A variety of human and rat cultured cells were examined for their ability to bind MVIIA OCT, to identify cell types which are rich in OCT receptor sites.

The human and rat cell types indicated at the right in Table 5 were grown in a culture medium containing 10% fetal bovine serum. Cells were frozen in medium containing 10% DMSO, stored in liquid nitrogen until use, and rapidly thawed and diluted 10 fold in phosphate buffered saline (20 mM sodium phosphate, 150 mM NaCl, pH 7.4). All procedures were carried out at 4° C. The cells were then centrifuged at 1300×g for 10 min. The supernatant was decanted, and the cells were resuspended in 3 volumes (relative pellet volume) distilled water. The cells were broken and homogenized using a Polytron mixer (10 seconds), then centrifuged at 24,500×g for 10 min. The resulting membrane pellet was resuspended in 3 volumes distilled water, and used in the binding assay. Protein concentrations were estimated using the BioRad protein assay reagent.

For binding, cells were suspended in a mixture containing 20 mM HEPES buffer pH 7.4, 0.1 mM EDTA, 0.1 mM EGTA, (PMSF), 2 uM leupeptin, 1 uM pepstatin, 125 mM NaCl, 0.1% gelatin. Radiolabeled MVIIA OCT was added at a concentration of 1 nM. Nonspecific binding was estimated by inclusion of 3 uM unlabeled MVIIA in replicate tubes. The results are shown in Table 5 below.

TABLE 5

| | (fmol/mg. prot.) | Cell Type |
|---|---|---|
| Kelly | 44.7 | Human neuroblastoma |
| NG-108 | 45.6 | Rat glioma x mouse neuroblastoma |
| IMR-32 | 369.1 | Human neuroblastoma |
| SKNSH | 27.1 | Human neuroblastoma |
| SY5Y(−RA)[a] | 46.8 | Human neuroblastoma |
| SY5Y(+RA)[a] | 135.4 | Human neuroblastoma |
| PC-12(−NGF)[b] | 56.6 | Rat pheochromocytoma |
| PC-12(−NGF)[b] | 79.1 | Rat pheochromocytoma |
| 293 | <4.6 | Human kidney |

EXAMPLE 7

Inhibition of Ionic Currents

Ionic currents through calcium channels were examined in cells that were voltage-clamped by a single patch-clamp electrode. These whole-cell patch-clamp studies were performed mainly on N1E115 mouse neuroblastoma cells, although a variety of cell types have been examined.

A. Current Measurement Methods

Most measurements were obtained using a bath saline that allowed examination of the calcium currents in the absence of other ionic currents. These solutions contained 80 mM NMDG (as a sodium replacement), 30 mM TEACl (to block potassium currents), 10 mM $BaCl_2$ (as a charge-carrier through the calcium channels), and 10 mM HEPES at pH 7.3. Some solutions also contained 2 mM quinidine (to block potassium currents) and 3 $\mu$M tetrodotoxin (to block sodium currents). Normal bath saline was (mM): 140 NaCl, 10 glucose, 3 KCl, 2 $CaCl_2$, 1 $MgCl_2$, 10 mM HEPES pH 7.3. Intracellular solutions contained 150 mM CsCl, 0.5 mM $CaCl_2$, 5 mM EGTA, 5 mM $MgCl_2$, 2 mM $K_2ATP$ at pH 7.3–7.4. Bath saline and all internal solutions were filtered before use.

Pipets were made from Corning 7052 glass (Garner Glass Company, Claremont, Calif. 91711), coated with Sylgard (Dow Corning, Midland, Mich. 48640) and fire-polished before use. Bubble numbers were typically 5 to 6, with pipet resistances typically 2–5 MOhms. Corning 8161, Kimble, and other glasses were also used without noticeable effect on the calcium currents observed.

Recordings were carried out at room temperature with an Axopatch 1-C amplifier (Axon Instruments, Foster City, Calif. 94404) and analyzed with pCLAMP software (Axon Instruments). Data were filtered at 1000 Hz for a typical sampling rate of 0.1 kHz; in all cases data was filtered at a frequency at most 1/5 of the sampling rate to avoid aliasing. Data were collected on-line by the software. Analysis was performed on-screen with print-out via a Hewlett-Packard LaserJet Printer (Hewlett-Packard, Palo Alto, Calif. 94306).

The typical experiment was conducted as follows: after seal formation followed by series resistance compensation and capacitative transient cancellation, a voltage clamp protocol was performed wherein the cell potential was stepped from the holding potential (typically −100 mV) to test potentials that ranged from −60 mV to +20 mV in 10 mV increments. The cell was held at the holding potential for 5 seconds between pulses. Protocols starting from other holding potentials usually covered the same range of test potentials.

B. Current Inhibition Measurement

FIG. 5A shows a calcium current trace from an N1E115 mouse neuroblastoma cell. The figure is read from left to right, with downward deflections of the trace indicating positive current flowing into the cell. Currents were elicited by a voltage step from −100 mV to −20 mV. The cell was bathed in saline with sodium replaced by NMDG and 10 mM Ba instead of 2 mM Ca. Potassium currents were blocked by TEA in the bath and Cs in the pipet solution.

The three traces in FIGS. 5B–5C show decreasing calcium currents, with increasing OCT peptide concentrations of 10 nM (5B), 50 nM (5C), and 200 nM (5D). The response of voltage-gated calcium current to increasing dosages of OCTs MVIIA and GVIA are shown in FIG. 6. The calculated ED50 is 12 nM for GVIA and 115 nM for MVIIA. These values indicate extremely high specificity of the pep ides for their site of action.

EXAMPLE 8

Inhibition of ATP Release from Fish Synaptosomes

Electric-ray, electric-organ (fish) synaptosomes were prepared substantially as described in Example 4. The diluted synaptosome suspension from the final centrifugation step was pelleted at 30,400×g for 15 min and resuspended in 1 ml of PBS (with the inclusion, for some experiments, of 1% BSA to enhance stability of the synaptasomes). This final synaptosome preparation was stored at 0° C. and used for ATP release experiments within 30 hours. Storage for longer periods resulted in the almost complete loss of depolarization-dependent ATP release activity.

Luminometry was performed by the method of Morel et al. (Morel), as modified by Schweitzer. Into a 5 ml polypropylene test tube were mixed 465 $\mu$l PSB, 5

μl of 5 μg/ml luciferin in PSB, 20 μl firefly lantern extract (1 Sigma FLE-50 bottle reconstituted in 1 ml PSB and spin- dialyzed through 3 ml of Sephadex G-25 pre-equilibrated in PSB), 5 μl 100 mM $CaCl_2$, and 5 μl synaptosome suspension (5–7 mg/ml protein, excluding BSA). The tube was placed in the chamber of a custom-built luminometer and the light output produced by extracellular ATP was continuously monitored by a chart recording of the voltage generated by the photomultiplier tube. Exocytotic release of ATP was evoked by injecting 0.5 ml of high K+ buffer (PSB with equimolar replacement of Na+ by K+) into the reaction mixture in the luminometer.

ATP release was quantitated by comparing the peak heights of unknowns with the heights of peaks generated by ATP standards that were injected into each reaction mixture at the end of each trial. Over the range investigated, light output was linear with respect to the amount of ATP injected.

The results obtained are given in Table 6 below for neurotransmitter (ATP) release from synaptosomes prepared from electric organ of *Ommata discopyge.*

TABLE 6

| Compound | $IC_{50}$ |
|---|---|
| MVIIA | 30 nM |
| GVIA | 200 nM |

EXAMPLE 9

Mouse Shaking Test for OCTs

Male Swiss-Webster mice were given intracerebral (IC) injections of MVIIA, GVIA, or SVIA, or its vehicle, at doses between 0.01–10.0 ug/animal. During the ICV injection the animal was unanesthesized, using a method previously described (Haley and McCormick, 1956). Animals were observed for the presence or absence of shaking behavior 15 minutes following injection. The percentage of animals exhibiting this behavior is shown in Table 7.

TABLE 7

| OCT | dose | n | percent "shakers" |
|---|---|---|---|
| vehicle | 0.0 | 100 | 4.0 |
| MVIIA | .01 | 30 | 23.3 |
| | .03 | 60 | 31.7 |
| | .1 | 60 | 60.0 |
| | .3 | 50 | 78.0 |
| | 1.0 | 10 | 100 |
| GVIA | .01 | 10 | 20.0 |
| | .03 | 30 | 60.0 |
| | .1 | 30 | 63.0 |
| | .3 | 10 | 90.0 |
| SVIA | .01 | 10 | 0.0 |
| | .03 | 10 | 10.0 |
| | .1 | 20 | 0 |
| | .3 | 20 | 0 |
| | 1.0 | 20 | 10 |
| | 3.0 | 30 | 13.3 |
| | 10.0 | 10 | 10 |

EXAMPLE 10

Reduction in Anatomical Damage: 1

A. Global Ischemia

Global ischemic damage was examined in the gerbil model, according to standard procedures (Kirino). Male mongolian gerbils (*Meriones unguiculatus,* Tumblebrook Farm, West Brookfield, Mass.) weighing 50–80 g were anesthetized in a small chamber with 4% halothane carried by 70% nitrous oxide (0.44 L/min) and 30% oxygen (0.19 L/min). They were then maintained throughout surgery with 2% halothane by placing their noses through a hole in a rubber dam on a gas delivery tube. Using aseptic techniques, both common carotid arteries were exposed, dissected free of surrounding tissue, and occluded with microvascular clamps approximately 3 to 4 mm above the clavicle. The occlusions were maintained for 8 minutes, timed while both arteries were occluded. There was generally a period of approximately 1 minute between clamping of each of the two arteries, and approximately 4 seconds between unclamping them. After the clamps were removed, the skin was sutured shut and anesthesia discontinued.

During or after the occlusion, an intracerebroventricular (ICV) injection aimed at the lateral ventricle was made. To accomplish this, a 10 microliter Hamilton syringe with a 27 gauge needle was filled with injectate by backloading to assure the absence of air in the system. A stiff plastic sleeve was slipped onto the needle so that 3.5 mm of the needle protruded past the sleeve. The skull around the bregma was exposed, a distance of 1.1 mm left of the midline was measured with a compass, and a distance of 0.4 mm posterior to bregma was approximated by eye. The needle tip was held perpendicular to the skull and inserted through it at that point by applying gentle pressure while twisting. It was advanced until the sleeve abutted the skull, and 5 microliters of injectate was infused over a period of approximately 3 sec. The skin was then sutured shut. Occluded animals received either drug or its vehicle. Injected, unoccluded controls were anesthetized, and received the ICV injection only.

B. Histological Examination of Gerbil brains

Animals were anesthetized with $CO_2$. The chest cavity was opened and the animal was perfused through the heart with approximately 3 milliliters of phosphate-buffered saline (PBS; 0.10M sodium phosphate; 0.15M sodium chloride) containing heparin (10 Units/ml), followed by approximately 10 ml of Zamboni's fix (15% (vol/vol) picric acid 4% (wt/vol) paraformaldehyde in 0.1M phosphate buffer pH 7.4. Brains were removed and left immersed in the same fixative for several hours.

Brains were blocked just posterior to the optic chiasm and posterior to the mammillary bodies. They were then placed in 10% (wt/vol) sucrose in PBS overnight at 4° C. The block containing the hippocampus was frozen with liquid Freon onto a cryostat chuck using Tissue-Tek® O.C.T. embedding medium for frozen tissue specimens (Miles Inc., Elkhart, IA). Sections 10 microns in thickness were cut. Series of 5 sections were collected, with each series approximately 100 microns apart, until the relevant part of the hippocampus was obtained (40–50 sections per brain). At least 8 sections per brain were stained with hematoxylin and eosin, substantially according to reported procedures.

Coverslips were then placed over the sections, using Permount™ as an adhesive. FIGS. 7A and 7B are low-power micrographs of gerbil hippocampus (CA) in animals after ischemia, after infusion of MVIIA OCT (7A) or after drug vehicle (7B). The arrows in the figures indicate the approximate borders of the CA. At higher power, cells in the drug-treated ischemic animals appear normal (FIG. 8A), whereas damage is apparent in the ischemic animals receiving vehicle alone (FIG.

8B). Another example of complete drug protection is seen in FIG. 8C, and an example of partial protection is seen in FIG. 8D, where there are a small number of damaged cells.

Sections, such as those seen in FIGS. 7 and 8, were viewed and scored by an investigator having no knowledge of the treatment of any particular sample. Ischemic damage was scored in the CA-1 region of the hippocampus. Damage was generally seen as pink (eosinophilic) cytoplasm and shrunken, dark blue nuclei. Scoring was as described below:

| Score | Observation |
|---|---|
| 0 | No damaged cells were apparent. |
| 1 | Less than 25% damaged cells in a CA field, or damage was restricted to the extreme edges of the CA 1 region. |
| 2 | Approximately 50% damaged cells in a CA 1 field, or damage to less than half the length of CA 1. |
| 3 | Damaged cells outnumber normal cells to a maximum of 75%, with damage extending throughout most of CA 1. |
| 4 | Complete damage to CA 1, with fewer than 25% normal cells surviving. |

The extent of anatomical damage in ischemic animals treated with MVIIA or GVIA OCT or receiving vehicle alone (control), based on the above scoring system, is given in Table 8 below. The peptide was administered by ICV infusion during the eight minutes of occlusion, at a total dose indicated in the table below. As seen, the extent of damage in the higher-dose MVIIA OCT treated animal was only 25% of that in untreated animals. The GVIA peptide also produced more than a 50% reduction in damage, and the lower dose was near maximal effectiveness.

TABLE 8

| Treatment | N | Mean score (S.E.M) | Percent Damage |
|---|---|---|---|
| Vehicle | 20 | 3.1 (.32) | 100% |
| 0.02 ug MVIIA | 4 | 1.9 (.83) | 61% |
| 0.1 ug MVIIA | 18 | 0.8 (.09)*** | 25% |
| 0.02 ug GVIA | 3 | 1.3 (.33)* | 42% |
| 0.1 μg GVIA | 11 | 1.2 (.39)** | 39% |

*p< .05 compared to vehicle (Student's T-test)
**p< .005 compared to vehicle (Student's T-test)
***p<.0005 compared to vehicle (Student's T-test)

In a second treatment method, the OCT peptide was administered by ICV infusion 1 hour after the 8-min occlusion, at the same drug dosage level as indicated above. The anatomical damage in the presence and absence of drug, scored as above, is given in Table 9 below. A comparison of the data in Table 8 indicates little loss of protective effect at a comparable dose (0.1 μg) when the drug is administered 1 hour after the ischemic event (8 min of occlusion).

TABLE 9

| Treatment | N | Mean score (S.E.M) | Percent Damage |
|---|---|---|---|
| Vehicle | 15 | 3.0 (.31) | 100% |
| 0.1 μg MVIIA | 16 | 0.9 (.13)*** | 30% |
| 0.3 μg MVIIA | 3 | 0.7 (.17)** | 23% |

**p< .005 compared to vehicle (Student's T-test)
***p<.0005 compared to vehicle (Student's T-test)

EXAMPLE 11

Reduction in Anatomical Damage: 2

A. Global Ischemia

Global ischemic damage was examined in the rat brain model, employing the four-vessel occlusion method of Pulsinelli and Brierly (Pulsinelli) for introducing temporary global ischemia in rats. Although the two carotid arteries supply blood to the forebrain, their occlusion alone has only moderate effects on forebrain blood flow because the posterior communicating arteries allow blood to be shunted from the brainstem blood supply, which is fed by the two vertebral arteries. Therefore, in order to effect severe forebrain ischemia, all four vessels must be occluded. The procedure used allows ischemia to be produced in conscious animals, by closing surgically implanted clamps, and therefore avoid possible interactions with drug treatment. The procedure was modified to allow carotid occlusion without the need for reopening a skin wound in conscious animals.

Surgery was performed to permanently occlude both vertebral arteries and to implant an arterial clasp to allow temporary occlusion of the carotid arteries at a later time. Under sodium pentobarbital anesthesia (60 mg/kg) male Fisher 344 rats were placed in a sterotaxic holder and the first cervical vertebra was exposed with the aid of a dissecting microscope. The vertebral arteries were occluded through the alar foramina with a thermocautery device and the skin closed with wound clips. The animal was placed on its back and the carotid arteries were carefully dissected free of the surrounding nerves and vessels under the microscope. The loose end of the Silastic loop of the clasp was passed behind the artery and put through the open side of the clasp and secured as for the other end. This was then repeated for the other carotid. The clasps were tied into the skin with 3-0 suture as the skin was closed so as to externalize the ends of the loop. Ischemia was produced 4 days after surgery. To occlude the carotid arteries, the animal was held by lightly pinching the skin at the back of the neck and the ends of each loop were pulled out and secured with a bulldog clamp. At the end of the 15 min occlusion, the clamps were removed to allow reperfusion. An effective occlusion causes the animal to lose its righting response (RR) within about 1 min of occlusion. When the animal does not lose the RR or regains it during occlusion, the loops are pulled tighter to assure complete carotid occlusion. Animals that do not lose their RR are eliminated from the study, because this suggests that there is still significant cerebral blood flow.

Neuropathological analysis (see below) of such animals confirms this because the damage is less than in animals that do lose their RR. Some animals right themselves once or twice during the occlusion, but immediately lose the RR again, and are not eliminated from the study. An animal that rights itself and remains up is eliminated.

Immediately following reperfusion, rats were anesthetized with halothane (as for gerbils) and 0.3 μg MVIIA OCT in 5 μL saline (n=7) or saline alone (n=5) was injected into the lateral ventricle as for gerbils. The coordinates were 1.2 mm left of midline and 0.5 mm posterior to bregma. Rectal temperature was monitored from just before occlusion until the end of the day.

Neuropathologic analysis was conducted in a manner similar to that described for gerbils, with the results shown in Table 10.

TABLE 10

| Treatment | N | Mean score (S.E.M) |
|---|---|---|
| vehicle | 4 | 3.6 (0.38) |
| MVIIA OCT (0.3 μg) | 5[a] | 1.2 (0.36)** |

[a]Animals give OCT MVIIA ICV were included in the study only if they exhibited characteristic shaking behavior.
**$p < .005$ unpaired Student's t test.

As seen from the data, treatment with MVIIA OCT reduced anatomical damage to about ⅓ that seen in the absence of peptide treatment.

EXAMPLE 12

Protection Against Loss of Functional Activity

A. Hyperactivity

One common sequence of cerebral ischemia is hyperactivity, which can be seen as pacing behavior within a few hours of occlusion and can be measured up to several days later. Hyperactivity was quantitated with Automex activity monitors (Columbia Instruments, Columbus, Ohio), which record perturbations of a radiofrequency field. Gerbils were tested individually in 17×27-cm plastic cages for 60 min, with cumulative activity counts recorded every 15 min for statistical analysis. Baseline activity was measured before surgery to ensure comparability of the different treatment groups on this measure. FIG. 9 shows the activity counts measured at 0, 1 and 3 days after occlusion, over a 60-minute period each. Occluded animals are indicated by triangles; non-occluded by circles; untreated, by open symbols; and administration of MVIIA by closed symbols.

B. Spontaneous Alternation

Short-term memory changes in gerbils were tested in a Y maze, in which the animal is placed in the base of the stem of the maze, and when the animal enters an arm, a door is shut behind it. After 5 sec, the gerbil is returned to its home cage for an intertrial interval (ITI) of 2 to 12 min. At the end of that interval the gerbil is run in the maze again in the same way. Most normal animals will alternate, that is, will enter the arm that was not entered on the first trial. Occasionally an animal did not enter an arm within about 1 min because it had had a seizure, so it was eliminated from that test.

Because individual experiments include too few animals per group to allow meaningful statistical evaluation of the data, the results were combined for all experiments in which there was good evidence of protection by drug treatment against hippocampal damage (Example 10). Only experiments with positive results were combined to determine if the anatomical protection was associated with behavioral protection.

Results of the spontaneous alternation tests are summarized in Table 11 for experiments in which there was anatomical protection from doses of at least 0.1 μg of either compound. A chi square test on the combined data was significant at $p<0.01$. Combining treatment groups to examine each factor separately (e.g., all occluded vs. all unoccluded, regardless of drug treatment) indicated that each was significant by chi square at $p<0.05$; that is, (a) ischemia caused worse performance and (b) the level of performance was largely restored in treated animals

TABLE 11

| | | Gerbils Alternating (Y) or Repeating (N) Experminents | | | | | | | | | |
|---|---|---|---|---|---|---|---|---|---|---|---|
| | | 3 | | 4 | | 5 | | 6 | | Combined | |
| Ischemia | Drug* | Y | N | Y | N | Y | N | Y | N | Y | N |
| No | No | 9 | 3 | 2 | 2 | 3 | 3 | 6 | 2 | 20 | 10 |
| | Yes | — | — | 4 | 0 | 5 | 1 | 4 | 0 | 13 | 1 |
| Yes | No | 2 | 6 | 4 | 4 | 4 | 4 | 3 | 4 | 13 | 18 |
| | Yes | 4 | 3 | 5 | 2 | 7 | 1 | 7 | 4 | 23 | 10 |

*Drug doses are from 0.1 to 0.3 μg of MVIIA or GVIA.

Although the invention has been described with respect to particular treatment methods and composition, it will be apparent to those skilled that various changes and modifications can be made without departing from the invention.

It is claimed:

1. A method of treating an ischemic condition in a mammalian subject, comprising
administering a binding/inhibitory omega-conotoxin peptide to the subject in a pharmaceutically effective amount, and
by said administering, reducing neuronal damage related to the ischemic condition.

2. The method of claim 1, wherein the peptide provides effective protection against loss of functional brain activity.

3. The method of claim 2, wherein the peptide provides effective protection against loss of short-term memory.

4. The method of claim 1, wherein the peptide is characterized by specific binding to omega-conotoxin binding sites associated with calcium channels in neuronal-cell membranes, as evidenced by competitive inhibition of omega-conotoxin binding to electric-ray electric organ or rat brain synaptosomes.

5. The method of claim 4, wherein the peptide has a $pK_i$, as measured by competitive displacement of MVIIA omega-conotoxin from electric-ray electric organ synaptosomes, of at least about 6.

6. The method of claim 1, wherein the peptide is characterized by specific inhibition of voltage-gated calcium currents selectively in neuronal tissue, as evidenced by inhibition of voltage gated calcium currents in cultured mouse neuroblastoma cells, but not voltage-gated calcium currents in muscle cells, such as cultured dissociated guinea pig cardiac ventricular muscle cells.

7. The method of claim 6, wherein the peptide has an $IC_{50}$ value, as measured by the inhibition of N1E115 mouse neuroblastoma cells, of less than about 1 μM.

8. The method of claim 7, wherein said $IC_{50}$ value is less than about 200 nM.

9. The method of claim 1, wherein the peptide is inhibitory with respect to neurotransmitter release selectively in neuronal tissue, as evidenced by inhibition of induced ATP release from electric-ray electric organ synaptosomes, but not with respect to neurotransmitter release at a mammalian neuromuscular junction to skeletal muscle.

10. The method of claim 1, wherein the peptide is characterized by:
(a) specific binding to omega-conotoxin binding sites associated with calcium channels in neuronal-cell membranes, as evidenced by competitive inhibition of omega-conotoxin binding to fish or rat brain synaptosomes;

(b) inhibition of voltage-gated calcium currents selectively in neuronal tissue, as evidenced by inhibition of voltage gated calcium currents in cultured mouse neuroblastoma cells, but not voltage-gated calcium currents in cultured rat muscle cells; and (c) inhibition of neurotransmitter release selectively in neuronal tissue, as evidenced by inhibition of induced ATP release from electric-ray electric organ synaptosomes, but noninhibition of neurotransmitter release at a mammalian neuromuscular junction to skeletal muscle.

11. The method of claim 1, wherein the peptide is further characterized by its ability to induce shaking in mice, following injection into mouse cerebro-spinal fluid.

12. The method of claim 1, wherein the peptide is selected from the group of binding/inhibitory G-group omega-conotoxin peptides consisting of GVIA, GVIIA, and RVIA, including binding/inhibitory analogs thereof.

13. The method of claim 12, wherein the peptide is GVIA.

14. The method of claim 10, wherein the peptide is selected from the group of binding/inhibitory M-group omega-conotoxin peptides consisting of MVIIA, MVIIB, and SVIB.

15. The method of claim 12, wherein the peptide is MVIIA.

16. The method of claim 13, wherein the peptide is further characterized by the following NMR-NOE based interatomic distances of about 4.5 angstrom (long-range) and 2.5 angstrom (short-range) between protons of the designated amino acid residue amide nitrogen, or as otherwise specified:

Long-range:
Lys (position 2) and Cys (position 16)
Gly (position 5) and Cys (position 28)
Lys (position 26) and Cys (position 20)
alpha H Cys (position 28) and Gly (position 18)
beta H Cys (position 28) and Lys (position 2)
alpha H Lys (position 26) and Cys (position 8)
beta H Cys (position 1) and Cys (position 16)
beta H Cys (position 28) and Gly (position 5)
beta H Cys (position 28) and Gly (position 18)

Short-range:
Ser (position 24) and Gly (position 25)
Asp (position 14) and Cys (position 15)
Tyr (position 13) and Asp (position 14)
Gly (position 25) and Lys (position 26).

17. The method of claim 1, wherein the peptide has an isoelectric point between about 10.5 and 12.

* * * * *